US012473590B2

(12) United States Patent
Okereke et al.

(10) Patent No.: US 12,473,590 B2
(45) Date of Patent: Nov. 18, 2025

(54) DETECTION OF MICROORGANISMS IN THE ESOPHAGUS

(71) Applicant: Board of Regents, The University of Texas System, Austin, TX (US)

(72) Inventors: Ikenna Okereke, Galveston, TX (US); Richard Pyles, Galveston, TX (US); Aaron Miller, Galveston, TX (US); Catherine Hamilton, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 300 days.

(21) Appl. No.: 17/375,966

(22) Filed: Jul. 14, 2021

(65) Prior Publication Data

US 2022/0017946 A1 Jan. 20, 2022

Related U.S. Application Data

(60) Provisional application No. 63/052,718, filed on Jul. 16, 2020.

(51) Int. Cl.
*C12Q 1/686* (2018.01)

(52) U.S. Cl.
CPC ........ *C12Q 1/686* (2013.01); *C12Q 2600/112* (2013.01)

(58) Field of Classification Search
CPC ......................... C12Q 1/686; C12Q 2600/112; C12Q 1/6886; C12Q 1/689
See application file for complete search history.

(56) References Cited

U.S. PATENT DOCUMENTS 4,683,195 A 7/1987 Mullis et al.
4,683,202 A 7/1987 Mullis

OTHER PUBLICATIONS

Morita, E., Narikiyo, M., Yano, A., Nishimura, E., Igaki, H., Sasaki, H., Terada, M., Hanada, N., & Kawabe, R. (2003). Different frequencies of *Streptococcus anginosus* infection in oral cancer and esophageal cancer. Cancer science, 94(6), 492-496. https://doi.org/10.1111/j.1349-7006.2003.tb01471.x (Year: 2003).*

(Continued)

*Primary Examiner* — Neil P Hammell
*Assistant Examiner* — Morgan Taylor Lindgren Baltzel
(74) *Attorney, Agent, or Firm* — Edwin S. Flores; Daniel J. Chalker; Chalker Flores, LLP

(57) ABSTRACT

The present invention includes a method of detecting and treating a patient suspected of having Barrett's esophagus comprising: obtaining a biological sample from an esophagus of the patient; determining a microbiome in the biological sample by detecting the presence of bacteria by plasmid dilution verification or quantitative polymerase chain reaction (qPCR); wherein if the patient has a microbiome indicative of an increased risk of esophageal cancer threating the patient with at least one of: removing at least part of the esophagus, esophagectomy probiotic therapy, or chemically targeting elimination of bacteria indicative of an increased risk of esophageal cancer.

13 Claims, 13 Drawing Sheets

- ESOPHAGEAL MICROBIOME (EMB) qPCR ARRAY

| | | | | | |
|---|---|---|---|---|---|
| *ACTINOMYCES* | *LACTOBACILLUS* | *ROTHIA MUCILAGINOSA* | *CAMPYLOBACTER* | *LAUTROPIA* | SAL 337 |
| *CAMPYLOBACTER CONCISUS* | *LEPTOTRICHIA* | *STREPTOCOCCUS ANGINOSIS* | *CAMPYLOBACTER SHOWAE* | *LEPTOTRICHIA WADEI* | *STREPTOCOCCUS MUTANS* |
| *CAPNOCYTOPHAGA* | *MYCOPLASMA FAUCIUM* | *STREPTOCOCCUS ORALIS* | *CORYNEBACTERIUM* | *NEISSERIA* | *STREPTOCOCCUS PNEUMONIAE* |
| *DIALISTER* | *PORPHYROMONAS ENDODONTALIS* | *STREPTOCOCCUS SALIVARIUS* | *FILIFACTOR ALOCIS* | *PORPHYROMONAS GINGIVALIS* | *STREPTOCOCCUS SANGUINIS* |
| *FUSOBACTERIUM NUCLEATUM* | *PREVOTELLA DENTICOLA* | *STREPTOCOCCUS THERMOPHILUS* | *FUSOBACTERIUM PERIODONTICUM* | *PREVOTELLA INTERMEDIA* | *STREPTOCOCCUS VESTIBULARIS* |
| *GAMELLA SANGUINIS* | *PREVOTELLA MELANINOGENICA* | *STREPTOCOCCUS* | *HAEMOPHILUS HAEMOLYTICUS* | *PREVOTELLA NIGRESCENS* | *VEILLONELLA* |
| *HAEMOPHILUS INFLUENZA* | *PREVOTELLA ORIS* | *VEILLONELLA ATYPICA* | *HAEMOPHILUS PARAHAEMOLYTICUS* | *PREVOTELLA PALLENS* | *VEILLONELLA PARVULA* |
| *HAEMOPHILUS* | *PREVOTELLA* | *HAEMOPHILUS PARAINFLUENZAE* | *PREVOTELLA TIMONENSIS* | TOTAL 16S | HUMAN GAPDH |

(56) References Cited

OTHER PUBLICATIONS

Baba Y, Iwatsuki M, Yoshida N, Watanabe M, Baba H. Review of the gut microbiome and esophageal cancer: Pathogenesis and potential clinical implications. Ann Gastroenterol Surg. Jun. 7, 2017;1(2):99-104. doi: 10.1002/ags3.12014. PMID: 29863142; PMCID: PMC5881342. (Year: 2017).*
D'Journo XB et al. (Current management of esophageal cancer. J Thorac Dis. May 2014;6 Suppl 2(Suppl 2):S253-64.). (Year: 2014).*
Snider, E. J., Compres, G., Freedberg, D. E., Khiabanian, H., Nobel, Y. R., Stump, S., Uhlemann, A. C., Lightdale, C. J., & Abrams, J. A. (2019). Alterations to the Esophageal Microbiome Associated with Progression from Barrett's Esophagus to Esophageal Adenocarcinoma. Cancer epidemiology, biomarkers (Year: 2019).*
Eluri S, Tappata M, Huang KZ, Koutlas NT, Robey BS, Fan C, Reed CC, Shaheen NJ, Dellon ES. Distal esophagus is the most commonly involved site for strictures in patients with eosinophilic esophagitis. Dis Esophagus. Mar. 5, 2020;33(2):doz088. doi: 10.1093/dote/doz088. PMID: 31778150; PMCID: PMC10060705. (Year: 2020).*
Plat VD, van Rossen TM, Daams F, de Boer NK, de Meij TGJ, Budding AE, Vandenbroucke-Grauls CMJE, van der Peet DL. Esophageal microbiota composition and outcome of esophageal cancer treatment: a systematic review. Dis Esophagus. Aug. 13, 2022;35(8):doab076. doi: 10.1093/dote/doab076. PMID: 34761269; PMCI (Year: 2022).*
Okereke et al. "Microbiota Detection Patterns Correlate With Presence and Severity of Barrett's Esophagus." Front Cell Infect Microbiol. Feb. 23, 2021;11:555072. doi: 10.3389/fcimb.2021.555072. PMID: 33708643; PMCID: PMC7942024. (Year: 2021).*
Zhang et al. "Insights Into the Oral Microbiome and Barrett's Esophagus Early Detection: A Narrative Review." Clin Transl Gastroenterol. Aug. 26, 2021;12(9):e00390. doi: 10.14309/ctg.0000000000000390. PMID: 34446641; PMCID: PMC83 (Year: 2021).*
Blankenburg, et al. "Manipulation of FASTQ data with Galaxy" Bioinformatics 2010;26:1783-85.
Amir et al. "Gastric microbiota is altered in oesophagitis and Barrett's oesophagus and further modified by proton bump inhibitors", Environmental Microbiology, 2014, 16(9).
Blackett et al., "Oesophageal bacterial biofilm changes in gastro-oesophageal reflux disease, Barrett's and oesophageal carcinoma: association or causality?", Aliment Pharmacol Ther 2013; 37: 1084-1092.
Deshpande et al., "Signatures within the esophageal microbiome are associated with host genetics, age, and disease", Deshpande et al. Microbiome (2018) 6:227.
Devaraj et al., "The Human Gut Microbiome and Body Metabolism: Implications for Obesity and Diabetes", Clinical Chemistry 59:4, 617-628 (2013).
Di Pietro et al., "Screening for Barrett's Esophagus", May 2015, Reviews in Basic and Clinical Gastroenterology and Hepatology.
Di Pilato et al., "The esophageal microbiota in health and disease", Ann. N.Y. Acad. Sci. ISSN 0077-8923.
Domper et al., "Esophageal cancer: Risk factors, screening and endoscopic treatment in Western and Eastern countries", World J Gastroenterol Jul. 14, 2015; 21(26): 7933-7943.
Elias et al., "The Role of Acid Suppression in Barrett's Esophagus", The American Journal of Medicine, vol. 130, No. 5, May 2017.
Yoku Hayakawa et al., "Gastrin and upper GI cancers", Elsevier, Current Opinion in Pharmacology 2016, 31:31-37.
Huang et al., "The Expensive-Tissue Hypothesis in Vertebrates: Gut Microbiota Effect, a Review", Int. J. Mol. Sci. 2018, 19, 1792; doi:10.3390.
Hvid-Jensen et al., "Incidence of Adenocarcinoma among Patients with Barrett's Esophagus", The New England Journal of Medicine, Oct. 13, 2011, vol. 365 No. 15.
Kaakoush et al., "The oesophageal microbiome: an unexplored link in obesity-associated oesophageal adenocarcinoma", FEMS Microbiology Ecology, 92, 2016, fiw161.
Kaakoush et al., "Cross-talk among metabolic parameters, esophageal microbiota, and host gene expression following chronic exposure to an obesogenic diet", Scientific Reports, 7:45753, DOI: 10.1038/srep45753.
Klindworth et al., "Evaluation of general 16S ribosomal RNA gene PCR primers for classical and next-generation sequencing-based diversity studies", Nucleic Acids Research, 2013, vol. 41, No. 1.
Langmead et al., "Fast gapped-read alignment with Bowtie2", Brief Communications; nature methods, vol. 9, No. 4, Apr. 2012, 357.
Jing Lv et al., "Alteration of the esophageal microbiota in Barrett's esophagus and esophageal adenocarcinoma", World J Gastroenterol, May 14, 2019; 25(18): 2149-2161.
Lynch et al., "The Human Intestinal Microbiome in Health and Disease", N Engl J Med, 375;24, Dec. 15, 2016.
Martinez et al., "Western diets, gut dysbiosis, and metabolic diseases: Are they linked?", Gut Microbes, 2017, vol. 8, No. 2, 130-142.
Mosavi-Jarrahi et al., Epidemiology of Esophageal Cancer in the High-Risk Population of Iran, Epidemiology of Esophageal Cancer in High Risk Areas of Iran, Asian Pacific Journal of Cancer Prevention, vol. 7, 2006.
Münch et al., High-Fat Diet Accelerates Carcinogenesis in a Mouse Model of Barrett's Esophagus via Interleukin 8 and Alterations to the Gut Microbiome, Gastroenterology 2019;157:492-506.
Okereke et al., "Associations of the microbiome and esophageal disease", Journal of Thoracic Disease, J Thorac Dis 2019;11(Suppl 12):S1588-S1593.
Okereke et al., "Microbiota of the Oropharynx and Endoscope Compared to the Esophagus", Scientific Reports | (2019) 9:10201.
Okereke et al., Microflora composition in the gastrointestinal tract in patients with Barrett's esophagus, Journal of Thoracic Disease, J Thorac Dis 2019;11(Suppl 12):S1581-S1587.
Paull et al., "Gastric and Esophageal Campylobacter pylori in Patients With Barrett's Esophagus", Gastroenterology 1988;95:216-8.
Pei et al., "Bacterial biota in the human distal esophagus", PNAS, Mar. 23, 2004, vol. 101, N. 12, pp. 4250-4255.
Joel E. Richter et al., "Presentation and Epidemiology of Gastroesophageal Reflux Disease", Gastroenterology 2018;154:267-276.
Peter D. Siersema, "Esophageal Cancer", Gastroenterol Clin N Am 37 (2008) 943-964.
Snider et al., "Potential Role of the Microbiome in Barrett's Esophagus and Esophageal Adenocarcinoma", Dig Dis Sci (2016) 61:2217-2225.
Snider et al. "Barrett's esophagus is associated with a distinct oral microbiome", Clinical and Translational Gastroenterology (2018) 9:135. Clinical and Translational Gastroenterology.
Theodorou et al., "Intraluminal pH and Goblet Cell Density in Barrett's Esophagus", J Gastrointest Surg (2012) 16:469-474.
Wani et al., "Diagnosis and Management of Low-Grade Dysplasia in Barrett's Esophagus: Expert Review From the Clinical Practice Updates Committee of the American Gastroenterological Association", Gastroenterology 2016;151:822-835.
Yang et al., "Inflammation and Intestinal Metaplasia of the Distal Esophagus Are Associated With Alterations in the Microbiome", Gastroenterology 2009;137:588-597.
Yang et al, "Microbiome in Reflux Disorders and Esophageal Adenocarcinoma", Cancer J. 2014 ; 20(3): 207-210. NIH Public Access.
Yilmaz et al., "The SILVA and "All-species Living Tree Project (LTP)" taxonomic frameworks", Nucleic Acids Research, 2014, vol. 42, Database issue D643-D648.
Zackular et al., "The Gut Microbiome Modulates Colon Tumorigenesis", Research Article, Nov./Dec. 2013 vol. 4 Issue 6 e00692-13.

* cited by examiner

FIGURE 1 - ESOPHAGEAL MICROBIOME (EMB) qPCR ARRAY

| | | | | | |
|---|---|---|---|---|---|
| *ACTINOMYCES* | *LACTOBACILLUS* | *ROTHIA MUCILAGINOSA* | *CAMPYLOBACTER* | *LAUTROPIA* | SAL 337 |
| *CAMPYLOBACTER CONCISUS* | *LEPTOTRICHIA* | *STREPTOCOCCUS ANGINOSIS* | *CAMPYLOBACTER SHOWAE* | *LEPTOTRICHIA WADEI* | *STREPTOCOCCUS MUTANS* |
| *CAPNOCYTOPHAGA* | *MYCOPLASMA FAUCIUM* | *STREPTOCOCCUS ORALIS* | *CORYNEBACTERIUM* | *NEISSERIA* | *STREPTOCOCCUS PNEUMONIAE* |
| *DIALISTER* | *PORPHYROMONAS ENDODONTALIS* | *STREPTOCOCCUS SALIVARIUS* | *FILIFACTOR ALOCIS* | *PORPHYROMONAS GINGIVALIS* | *STREPTOCOCCUS SANGUINIS* |
| *FUSOBACTERIUM NUCLEATUM* | *PREVOTELLA DENTICOLA* | *STREPTOCOCCUS THERMOPHILUS* | *FUSOBACTERIUM PERIODONTICUM* | *PREVOTELLA INTERMEDIA* | *STREPTOCOCCUS VESTIBULARIS* |
| *GAMELLA SANGUINIS* | *PREVOTELLA MELANINOGENICA* | *STREPTOCOCCUS* | *HAEMOPHILUS HAEMOLYTICUS* | *PREVOTELLA NIGRESCENS* | *VEILLONELLA* |
| *HAEMOPHILUS INFLUENZA* | *PREVOTELLA ORIS* | *VEILLONELLA ATYPICA* | *HAEMOPHILUS PARAHAEMOLYTICUS* | *PREVOTELLA PALLENS* | *VEILLONELLA PARVULA* |
| *HAEMOPHILUS* | *PREVOTELLA* | *HAEMOPHILUS PARAINFLUENZAE* | *PREVOTELLA TIMONENSIS* | TOTAL 16S | HUMAN GAPDH |

FIG. 1

VENN DIAGRAM SHOWING GENERA SIGNIFICANTLY RELATED TO PRESCENCE/ABSENCE OF BARRETT'S ESOPHAGUS AND LENGTH OF BARRETT'S COLUMN

FIG. 6A
FIG. 6B
FIG. 6C
FIG. 6D

FIG. 6

FIG. 6A

| TARGET | 10e7 AVG | 10e5 AVG | 10e3 AVG | 10e2 AVG | 10e1 AVG | NTC | 10e7 SD | 10e5 SD | 10e3 SD | 10e2 SD | 10e1 SD | 10e7 DETECT | 10e5 DETECT | 10e3 DETECT | 10e2 DETECT | 10e1 DETECT | NTC |
|---|---|---|---|---|---|---|---|---|---|---|---|---|---|---|---|---|---|
| ACTINOMYCES SPP | 22.40 | 28.13 | 37.33 | 37.91 | 37.98 | 38.00 | 1.15 | 0.19 | 0.71 | 0.19 | 1.10 | 100% | 100% | 100% | 75% | 100% | 100% |
| FUSOBACTERIUM NUCLEATUM | 20.21 | 25.89 | 35.53 | 37.12 | | | 1.42 | 0.33 | 0.62 | 0.85 | | 100% | 100% | 100% | 75% | 0% | 0% |
| LACTOBACILLUS SPP | 20.59 | 27.19 | 37.08 | 36.62 | | | 1.39 | 0.12 | 0.40 | | | 100% | 100% | 100% | 25% | 0% | 0% |
| PREVOTELLA DENTICOLA | 19.90 | 25.29 | 33.33 | 36.52 | | 36.17 | 0.72 | 0.15 | 1.04 | 2.07 | | 100% | 100% | 100% | 50% | 0% | 33% |
| ROTHIA MUCILAGINOSA | 20.54 | 25.95 | 34.15 | 36.74 | 35.42 | | 0.83 | 0.32 | 0.22 | | | 100% | 100% | 100% | 25% | 20% | 0% |
| STREPTOCOCCUS THERMOPHILUS | 19.07 | 24.71 | 33.00 | 34.44 | | | 0.87 | 0.12 | 0.45 | 1.03 | | 100% | 100% | 100% | 100% | 0% | 0% |
| CAMPLYLOBACTER -EMB | 19.22 | 24.72 | 33.23 | 35.47 | 35.22 | | 0.46 | 0.36 | 0.02 | 1.22 | | 100% | 100% | 100% | 50% | 20% | 0% |
| FUSOBACTERIUM PERIODONTICUM | 19.51 | 25.18 | 32.82 | 35.54 | 35.43 | | 0.46 | 0.26 | 0.87 | 0.45 | 0.23 | 100% | 100% | 100% | 50% | 40% | 0% |
| LAUTROPIA | 18.17 | 24.08 | 31.94 | 33.55 | 33.94 | | 0.52 | 0.13 | 0.46 | 0.25 | 0.07 | 100% | 100% | 100% | 75% | 40% | 0% |
| PREVOTELLA INTERMEDIA | 18.05 | 24.01 | 31.60 | 33.51 | | | 0.78 | 0.11 | 0.57 | 0.48 | | 100% | 100% | 100% | 50% | 0% | 0% |
| SAL 337 | 21.00 | 26.59 | 34.45 | 36.14 | | | 0.91 | 0.31 | 1.10 | 0.27 | | 100% | 100% | 100% | 50% | 0% | 0% |

TO FIG. 6B

FROM FIG. 6A

| | | | | | | | | | | | | | | | | | |
|---|---|---|---|---|---|---|---|---|---|---|---|---|---|---|---|---|---|
| STREPTOCOCCUS VESTIBULARIS | 18.84 | 24.85 | 33.08 | 34.24 | 34.96 | | 0.84 | 0.38 | 0.25 | 0.77 | | 100% | 100% | 100% | 100% | 20% | 0% |
| CAMPYLOBACTER CONSIUS | 20.22 | 26.65 | 36.17 | 37.24 | 38.12 | | 0.57 | 0.13 | 0.81 | | 1.09 | 100% | 100% | 100% | 25% | 40% | 0% |
| GEMELLA SANGUINIS | 19.07 | 25.11 | 34.92 | 33.61 | | | 0.40 | 0.12 | 0.42 | | | 100% | 100% | 100% | 25% | 0% | 0% |
| LEPTOTRICHIA -EMB | 18.46 | 24.18 | 32.52 | 35.10 | 34.65 | | 0.61 | 0.12 | 0.60 | 0.31 | 0.42 | 100% | 100% | 100% | 75% | 40% | 0% |
| PREVOTELLA MELANINOGENICA | 18.47 | 24.36 | 32.22 | 36.43 | 36.33 | | 0.61 | 0.37 | 0.60 | | 1.67 | 100% | 100% | 100% | 25% | 40% | 0% |
| STREPTOCOCCUS ANGINOSIS | 21.86 | 28.09 | 36.70 | 38.12 | | | 0.76 | 0.27 | 0.85 | 0.71 | | 100% | 100% | 67% | 50% | 0% | 0% |
| STREPTOCOCCUS UNIVERSAL | 18.05 | 24.03 | 30.93 | 32.71 | 33.86 | 35.72 | 0.56 | 0.20 | 0.29 | 1.61 | 1.28 | 100% | 100% | 100% | 100% | 100% | 100% |
| CAMPYLOBACTER SHOWAE | 18.78 | 24.89 | 32.33 | | 33.20 | | 0.50 | 0.34 | 0.44 | | | 100% | 100% | 100% | 0% | 20% | 0% |
| HAEMOPHILUS HAEMOLYTICUS | 19.33 | 25.13 | 33.13 | 36.28 | 36.49 | 35.20 | 0.44 | 0.30 | 0.83 | 0.59 | 1.89 | 100% | 100% | 100% | 50% | 80% | 33% |
| LEPTOTRICHIA WADEI | 18.35 | 24.37 | 32.76 | 34.12 | | | 0.51 | 0.41 | 1.10 | 1.25 | | 100% | 100% | 100% | 50% | 0% | 0% |
| PREVOTELLA NIGRESCENS | 18.97 | 25.55 | 33.52 | 36.53 | 38.32 | | 0.18 | 0.06 | 0.33 | 0.58 | | 100% | 100% | 100% | 75% | 20% | 0% |

TO FIG. 6C

FIG. 6B

FROM FIG. 6B

| | | | | | | | | | | | | | | | | | |
|---|---|---|---|---|---|---|---|---|---|---|---|---|---|---|---|---|---|
| STREPTOCOCCUS MUTANS | 17.62 | 23.98 | 32.15 | 34.70 | | | 0.66 | 0.10 | 2.07 | 1.71 | | 100% | 100% | 100% | 50% | 0% | 0% |
| VEILLONELLA | 18.75 | 24.90 | 32.11 | 34.83 | 37.28 | | 0.61 | 0.37 | 0.64 | 0.64 | 1.65 | 100% | 100% | 100% | 100% | 40% | 0% |
| CAPNOCYTOPHAGA SPP | 18.70 | 24.62 | 32.35 | 35.16 | | | 0.49 | 0.38 | 0.81 | | | 100% | 100% | 100% | 25% | 0% | 0% |
| HAEMOPHILUS INFLUENZAE | 24.36 | 30.01 | | | 36.09 | | 0.38 | 0.01 | | | | 100% | 100% | 0% | 0% | 20% | 0% |
| MYCOPLASMA FAUCIUM | 18.19 | 24.31 | 31.82 | 35.75 | | | 0.39 | 0.27 | 0.56 | 1.30 | | 100% | 100% | 100% | 50% | 0% | 0% |
| PREVOTELLA ORIS | 17.99 | 23.91 | 33.44 | 34.43 | | | 0.32 | 0.35 | 1.23 | 1.10 | | 100% | 100% | 100% | 100% | 0% | 0% |
| STREPTOCOCCUS ORALIS | 19.52 | 25.44 | 33.82 | 35.03 | | | 0.48 | 0.33 | 0.41 | 1.55 | | 100% | 100% | 100% | 75% | 0% | 0% |
| VEILLONELLA ATYPICA | 19.43 | 25.51 | 34.03 | 34.61 | | | 0.49 | 0.25 | 1.45 | 1.63 | | 100% | 100% | 100% | 50% | 0% | 0% |
| CORYNEBACTERIUM SPP | 17.99 | 23.74 | 31.41 | 32.69 | 34.95 | 33.72 | 0.44 | 0.40 | 1.07 | 0.74 | 1.56 | 100% | 100% | 100% | 50% | 40% | 100% |
| HAEMOPHILUS PARAHEAMOLYTICUS | 18.76 | 24.84 | 33.46 | 35.73 | | | 0.53 | 0.25 | 0.51 | 0.68 | | 100% | 100% | 100% | 75% | 0% | 0% |
| NEISSERIA - EMB | 19.60 | 25.60 | 34.98 | 35.14 | | | 0.27 | 0.38 | 1.80 | 0.20 | | 100% | 100% | 100% | 50% | 0% | 0% |
| PREVOTELLA PALLENS | 18.69 | 24.91 | 32.44 | 33.31 | 33.81 | | 0.61 | 0.16 | 0.91 | | | 100% | 100% | 100% | 25% | 20% | 0% |
| STREPTOCOCCUS PNEUMONIAE | 18.29 | 24.12 | 31.71 | 33.24 | 34.22 | | 0.68 | 0.20 | 0.47 | 0.83 | | 100% | 100% | 100% | 75% | 20% | 0% |

TO FIG. 6D

FIG. 6C

FROM FIG. 6C

| | | | | | | | | | | | | | | | | | |
|---|---|---|---|---|---|---|---|---|---|---|---|---|---|---|---|---|---|
| VEILLONELLA PARVULA | 17.45 | 23.39 | 31.76 | 32.36 | | 39.40 | 0.62 | 0.24 | 0.81 | 0.30 | | 100% | 100% | 100% | 75% | 0% | 33% |
| DIALISTER | 19.03 | 24.99 | 32.41 | 34.64 | 35.93 | 35.55 | 0.68 | 0.19 | 0.38 | 1.40 | 1.84 | 100% | 100% | 100% | 75% | 80% | 67% |
| HAEMOPHILUS PARAINFLUENZAE | 20.34 | 27.01 | 38.02 | 36.64 | | | 1.03 | 0.36 | 1.63 | | | 100% | 100% | 100% | 25% | 0% | 0% |
| PORPHYROMONAS ENDODONTALIS | 19.29 | 24.90 | 32.68 | 35.44 | | | 0.53 | 0.36 | 0.68 | 2.74 | | 100% | 100% | 100% | 100% | 0% | 0% |
| PREVOTELLA TIMONENSIS | 19.34 | 25.19 | 33.02 | 32.92 | | | 0.55 | 0.13 | 0.02 | 1.16 | | 100% | 100% | 100% | 50% | 0% | 0% |
| STREPTOCOCCUS SALIVARIUS | 19.00 | 25.09 | 32.85 | 34.98 | | | 0.33 | 0.26 | 1.01 | 1.16 | | 100% | 100% | 100% | 50% | 0% | 0% |
| 16S | 19.37 | 25.88 | 31.55 | 31.32 | 31.13 | 31.92 | 0.46 | 0.42 | 1.12 | 0.18 | 1.06 | 100% | 100% | 100% | 100% | 100% | 100% |
| FILIFACTOR ALOCIS | 21.20 | 28.16 | 37.41 | 38.59 | | | 0.90 | 0.29 | 0.59 | 0.42 | | 100% | 100% | 100% | 50% | 0% | 0% |
| HAEMOPHILUS UNIVERSAL | 17.87 | 24.05 | 31.17 | 33.79 | 31.00 | | 0.56 | 0.18 | 0.69 | | | 100% | 100% | 100% | 25% | 20% | 0% |
| PORPHYROMONAS GINGIVALIS | 18.92 | 24.91 | 32.13 | 31.99 | 36.67 | | 0.54 | 0.27 | 0.94 | 0.58 | | 100% | 100% | 100% | 75% | 20% | 0% |
| PREVOTELLA SPP | 16.69 | 22.76 | 30.30 | 33.10 | 34.02 | | 0.57 | 0.15 | 0.94 | 0.74 | | 100% | 100% | 100% | 100% | 20% | 0% |
| STREPTOCOCCUS SANGUINIS | 18.14 | 23.82 | 32.20 | 34.08 | | | 0.51 | 0.21 | 0.50 | | | 100% | 100% | 100% | 25% | 0% | 0% |
| hGAPDH | 24.76 | 30.37 | 36.05 | | 36.22 | | 0.52 | 0.13 | | | | 100% | 100% | 33% | 0% | 20% | 0% |
| TOTAL | 19.34 | 25.32 | 33.36 | 34.94 | 35.22 | 35.71 | 0.62 | 0.24 | 0.74 | 0.91 | 1.15 | 100% | 100% | 96% | 56% | 20% | 12% |
| SD | 1.57 | 1.57 | 1.86 | 1.69 | 1.91 | 2.32 | 0.25 | 0.11 | 0.43 | 0.59 | 0.62 | 0% | 0% | 18% | 29% | 29% | 30% |
| n | 3 | 3 | 3 | 4 | 5 | | | | | | | | | | | | |

FIG. 6D

DETECTION OF MICROORGANISMS IN THE ESOPHAGUS

CROSS-REFERENCE TO RELATED APPLICATIONS

This application claims priority to U.S. Provisional Application Ser. No. 63/052,718, filed Jul. 16, 2020, the entire contents of which are incorporated herein by reference.

STATEMENT OF FEDERALLY FUNDED RESEARCH

This invention was made with government support under TR001439 awarded by the National Institutes of Health. The government has certain rights in the invention.

TECHNICAL FIELD OF THE INVENTION

The present invention relates in general to the field of detection of microorganisms in the esophagus, and more particularly, to novel methods for determining the presence of Barrett's esophagus and cancer.

BACKGROUND OF THE INVENTION

Without limiting the scope of the invention, its background is described in connection with esophageal disease and cancer.

Barrett's esophagus is a metaplastic change of the distal esophageal mucosa from squamous to simple columnar cells[1]. It is a known risk factor for esophageal cancer[2-3], and patients with Barrett's esophagus are recommended to undergo periodic surveillance endoscopy examinations[4]. However, only 1 in 860 patients with Barrett's esophagus will ultimately develop esophageal cancer[5]. Therefore, determining which patients with Barrett's esophagus are at high risk for progression to malignancy would increase the cost effectiveness of surveillance.

The role of the esophageal microbiome in promoting or preventing disease is poorly understood. Several prior studies have shown a relationship between the microbiome and Barrett's esophagus[6-9]. However, these articles have been limited and did not examine multiple locations along the esophagus.

The microbiome has been increasingly associated with different disease processes, but its role in esophagus is largely unknown. What is needed is an understanding of the associations of the esophageal microbiota with Barrett's esophagus and methods for detecting and treating the same.

SUMMARY OF THE INVENTION

In one embodiment, the present invention includes a method of detecting and treating a patient suspected of having Barrett's esophagus comprising: obtaining a biological sample from an esophagus of the patient; determining a microbiome in the biological sample by detecting the presence of bacteria by plasmid dilution verification or quantitative polymerase chain reaction (qPCR); wherein if the patient has a microbiome indicative of an increased risk of esophageal cancer treating the patient with at least one of: removing at least part of the esophagus, esophagectomy, probiotic therapy, chemically targeting elimination of bacteria indicative of an increased risk of esophageal cancer or increasing the frequency of endoscopic surveillance. In one aspect, the absence of *Streptococcus salivarius, Actinomyces, Prevotella*, or *Dialister* is indicative of an increased risk of esophageal cancer. In another aspect, the absence of *Corynebacterium, Dialister, Gemella, Haemophilus, Leptotrichia, Neisseria, Prevotella, Rothia, Streptococcus, Veillonella* is indicative of worsened severity of Barrett's esophagus and an increased risk of esophageal cancer. In another aspect, the method further comprises stratifying patients based on the presence of bacteria in the uvula, proximal esophagus and distal esophagus. In another aspect, the biological sample is an esophageal swab and mucosal biopsies were obtained from the uvula, proximal esophagus and distal esophagus. In another aspect, a decrease in *Streptococcus vestibularis* is indicative of Barrett's esophagus. In another aspect, the detection of *Streptococcus mutans* at the uvula is indicative of Barrett's esophagus. In another aspect, the lack of detection of *Actinomyces*, and *Prevotella pallens* at the proximal esophagus is indicative of Barrett's esophagus. In another aspect, the lack of detection of *Dialister, Prevotella* unspecified, *Streptococcus salivarius, Streptococcus* unspecified at the distal esophagus is indicative of Barrett's esophagus. In another aspect, the biological sample is obtained from the distal esophagus and a length of a Barrett's column correlated with a level of Barrett's esophagus leading to esophageal cancer. In another aspect, the biological sample is a breath sample, a saliva sample, or a biopsy of the esophagus. In another aspect, the presence of Barrett's esophagus is determined without use of age, gender or presence of hiatal hernia as a factor or factors.

In one embodiment, the present invention includes a method of detecting and treating a patient suspected of having Barrett's esophagus by plasmid dilution verification or quantitative polymerase chain reaction (qPCR) comprising: obtaining one or more samples from one or more locations of an esophagus of the patient; extracting RNA from the one or more sample; performing an amplification reaction to obtain amplification products of the extracted RNA; analyzing the amplification products and comparing to a known, available database containing sequencing of each of the one or more microorganisms to determine which microorganisms are detected and at what quantities when compared to a standard having a known amount of an extracted RNA. In one aspect, the RNA is extracted with a lysis buffer, a homogenizer, or both. In another aspect, the RNA is reverse transcribed into DNA before the addition of the fusion primers. In another aspect, the method further comprises the steps for plasmid dilution verification of adding fusion primers linked to hyper-variable regions for one or more target microorganisms in the extracted RNA; mixing an equal concentration of plasmids of cloned targets on an array of microorganisms with the sample in a 1:5 to 5:1 ratio between the extracting and adding steps. In another aspect, the ratio is 4:1, 3:1, 2:1, 1:1, 1:2, 1:3, or 1:4. In another aspect, the sample and the plasmids are serially diluted from $10^7$ to 10 copies. In another aspect, the method further comprises establishing a dynamic range for quantification and a lower-limit-of-detection for each cloned target, wherein the amplification is a quantitative polymerase chain reaction (qPCR) and the amplification is by thermocycling.

In one embodiment, the present invention includes a method of determining an extent of disease progression in a patient suspected of having Barrett's esophagus comprising: obtaining a biological sample from one or more locations of an esophagus of the patient; determining a microbiome in the biological sample by detecting the presence of bacteria by plasmid dilution verification or quantitative polymerase chain reaction (qPCR) at the one or more locations of the esophagus of the patient; and matching the extent of Barrett's esophagus to disease progression by detecting the presence of microorganisms at the one or more locations of the esophagus that correlate with different levels of Barrett's esophagus disease progression; and if the patient has a microbiome indicative or early Barrett's esophagus disease then increasing a frequency of Barrett's esophagus disease surveillance from every 3 months to every three years in three-month increments; or if the patient has a microbiome indicative of advanced Barrett's esophagus treating the patient with at least one of: removing at least part of the esophagus, esophagectomy, probiotic therapy, chemically targeting elimination of bacteria indicative of an increased risk of esophageal cancer or increased frequency of endoscopic surveillance. In one aspect, the absence of *Streptococcus salivarius, Actinomyces, Prevotella*, or *Dialister* is indicative of an increased risk of esophageal cancer. In another aspect, the absence of *Corynebacterium, Dialister, Gemella, Haemophilus, Leptotrichia, Neisseria, Prevotella, Rothia, Streptococcus, Veillonella* is indicative of an increased severity of Barrett's esophagus. In another aspect, the method further comprises stratifying patients based on the presence of bacteria in the uvula, proximal esophagus and distal esophagus. In another aspect, the biological sample is an esophageal swab and mucosal biopsies were obtained from the uvula, proximal esophagus and distal esophagus. In another aspect, a decrease in *Streptococcus vestibularis* is indicative of Barrett's esophagus. In another aspect, the detection of *Streptococcus mutans* at the uvula is indicative of Barrett's esophagus. In another aspect, the lack of detection of *Actinomyces*, and *Prevotella pallens* at the proximal esophagus is indicative of Barrett's esophagus. In another aspect, the lack of detection of *Dialister, Prevotella* unspecified, *Streptococcus salivarius, Streptococcus* unspecified at the distal esophagus is indicative of Barrett's esophagus. In another aspect, the biological sample is obtained from the distal esophagus and a length of a Barrett's column correlated with a level of Barrett's esophagus leading to esophageal cancer. In another aspect, the biological sample is a breath sample, a saliva sample, a biopsy of the esophagus or a serum sample. In another aspect, the presence of Barrett's esophagus is determined without use of age, gender or presence of hiatal hernia as a factor or factors.

BRIEF DESCRIPTION OF THE DRAWINGS

For a more complete understanding of the features and advantages of the present invention, reference is now made to the detailed description of the invention along with the accompanying figures and in which:

FIG. 1 shows the organisms on an EMB array.

FIG. 6 is a table with the results for the limit of detection of the various bacteria.

DETAILED DESCRIPTION OF THE INVENTION

Figure 2:
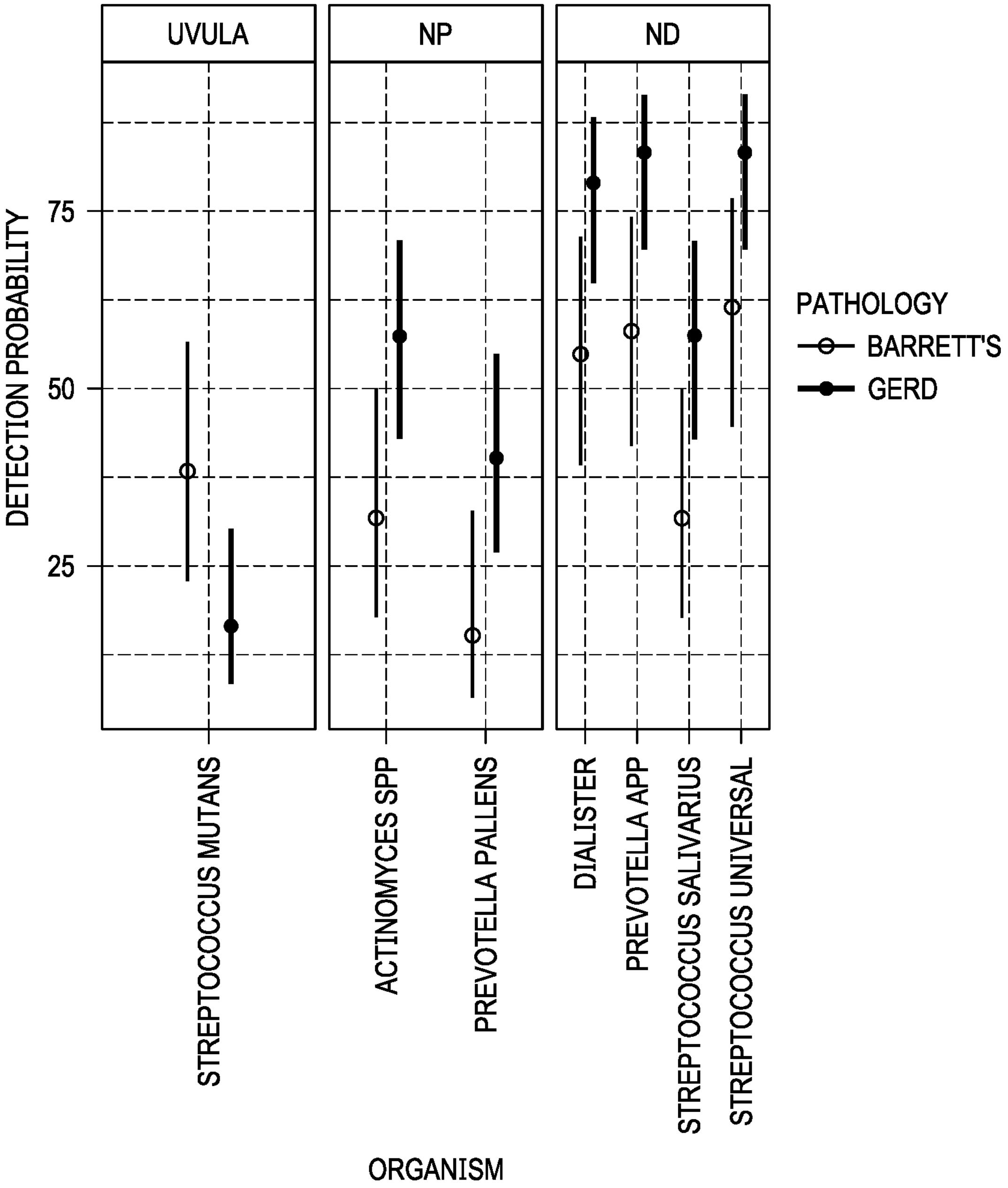
FIG. 2 shows organisms with significantly different detection rates at the uvula, proximal esophagus (NP) and distal esophagus (ND) in the Barrett's group compared to the GERD without Barrett's group.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not limit the invention, except as outlined in the claims.

The present invention provides for the detection of particular organisms affected by the presence and/or severity of Barrett's esophagus at different locations along the esophagus. Target organisms were identified, and data obtained using next generation sequencing of the 16S rRNA gene, followed by the development of a qPCR array (the Esophageal Microbiome Array; EMB) designed to evaluate greater than 85 percent of the detected species or genera in the analyzed samples.

The present invention determined whether the detection of particular organisms was affected by the presence and/or severity of Barrett's esophagus at different locations along the esophagus. Target organisms were identified from the literature and from data created using next generation sequencing of the 16S rRNA gene, followed by the development of a qPCR array (the Esophageal Microbiome Array; EMB) designed to evaluate greater than 85 percent of the detected species or genera in the analyzed samples.

As used herein, the term "amplification" refers to methods that include, but are not limited to, polymerase chain reaction (PCR), ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), rolling circle amplification (RCA), and invasive cleavage technology. These methods require a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme; etc. Thus, in general, a target nucleic acid is added to a reaction mixture that comprises the necessary amplification components, and a modified primer is formed.

These methods are known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

As used herein, the term "polynucleotide" refers to nucleic acid strands composed entirely of deoxyribonucleotides, entirely of ribonucleotides, or chimeric mixtures thereof. Polynucleotides may be comprised of internucleotide, nucleobase and sugar analogs. Unless denoted otherwise, whenever a polynucleotide sequence is represented, it will be understood that the nucleotides are in 5' to 3' orientation from left to right and that "A" denotes deoxyadenosine, "C" denotes deoxycytidine, "G" denotes deoxyguanosine, and "T" denotes thymidine.

As used herein, the term "polynucleotide template" refers to a region of a polynucleotide complementary to an oligomer, probe or primer polynucleotide. It is understood that a polynucleotide template will normally constitute a portion of a larger polynucleotide molecule, with the "template" merely referring to that portion of the polynucleotide molecule to which the oligomer, probe or primer of the present invention is complementary.

As used herein, the term "primer" refers to an oligonucleotide molecule that is complementary to a portion of a target sequence and, upon hybridization to the target sequence, has a free 3'-hydroxyl group available for polymerase-catalyzed covalent bonding with a 5'-triphosphate group of a deoxyribonucleoside triphosphate molecule, thereby initiating the enzymatic polymerization of nucleotides complementary to the template. Primers may include detectable labels for use in detecting the presence of the primer or primer extension products that include the primer.

As used herein, the term "probe" refers to a nucleobase oligomer that is capable of forming a duplex structure by complementary base pairing with a sequence of a target polynucleotide, and further where the duplex so formed is detected, visualized, measured and/or quantitated. In some embodiments, the probe is fixed to a solid support, such as in column, a chip or other array format. Probes may include detectable labels for use in detecting the presence of the probe.

As used herein, "target sequence" refers to a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction, a fragmentation reaction, and the like. A target sequence may be of any length. A target sequence often comprises a fragment of a target polynucleotide, and the length of that fragment may comprise some or all of the target polynucleotide from which it is derived.

As used herein, the term "template" refers to the region of the polynucleotide that constitutes the physical template for hybridization of another complementary polynucleotide. Templates may be genomic DNA, cDNA, PCR amplified DNA, or any other polynucleotide that serves as a pattern for the synthesis of a complementary polynucleotide.

The present invention may employ, unless otherwise indicated, conventional techniques of molecular biology, microbiology, recombinant DNA techniques, and oligonucleotide synthesis which are within the skill of the art. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2 d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of all of which are incorporated herein by reference.

Kits. The present invention also includes kits that include reagents that can be used in practicing the methods disclosed herein. The kits can include any reagent or combination of reagent discussed herein or that would be understood to be required or beneficial in the practice of the disclosed methods, including certain arrays. For example, the kits could include primers to perform the amplification reactions discussed in certain embodiments of the methods, as well as the buffers and enzymes required to use the primers as intended. The kit can also include a standard or custom array for detecting amplification products. For example, disclosed is a kit comprising reagents for real-time PCR-type amplification reaction for detecting a Barrett's esophagus microbiome, comprising sense primers, antisense primers and a nondegenerate probe. For example the kit can detect a microbiome of Barrett's esophagus.

For enhanced diagnostics, the present invention used a qPCR array to diagnose individuals with Barrett's esophagus microbiome changes and to monitor the success of therapeutic approaches. Another such array uses customized qPCR assays assembled into kitted systems for use in clinical microbiology facilities. The array can be used to identify optimal donated oral swab specimens from healthy donors to support development of therapeutic microbiome transplants. The therapeutic composition that include oral compositions, suppositories, enemas and/or serum samples that include supplementation with identified and cultured probiotic organisms reduced or lost in the microbiome of Barrett's esophagus patients.

The probiotic bacteria, prebiotic agents, and/or xenobiotics for use with the present invention can be provided in a variety of dosage forms. For example, e.g., tablets, capsules, pills, powders, granules, elixirs, tinctures, suspensions, syrups, enemas, suppositories, and emulsions may be used to provide the probiotic bacteria, prebiotic agents, and/or xenobiotics of the present invention to a patient in need of therapy for Barrett's esophagus.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

As used herein, the term "treatment" refers to the treatment of the conditions mentioned herein, particularly in a patient who demonstrates symptoms of Barrett's esophagus. As used herein, the term "treating" refers to any administration of a compound of the present invention and includes (i) inhibiting the disease in an animal that is experiencing or displaying the pathology or symptomatology of the diseased (i.e., arresting further development of the pathology and/or symptomatology) or (ii) ameliorating the disease in an animal that is experiencing or displaying the pathology or symptomatology of the diseased (i.e., reversing the pathology and/or symptomatology). The term "controlling" includes preventing, treating, eradicating, ameliorating or otherwise reducing the severity of the condition being controlled.

As used herein, the terms "effective amount" or "therapeutically effective amount" refer to an amount of a subject compound or probiotics that will elicit the biological or medical response to Barrett's esophagus that is being sought by the researcher, veterinarian, medical doctor or other clinician.

As used herein, the terms "administration of" or "administering a" when referring to a compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as oral, esophageal, intranasal, and the like; inhalation powders, sprays, suspensions, and the like.

Study Participants. After institutional review board approval was obtained (IRB #17-0215), 74 patients were included in the study. All authors had access to the study data and reviewed and approved the final manuscript. All participants were 1) patients undergoing surveillance endoscopy for a known history of Barrett's esophagus or 2) patients for whom screening endoscopy was recommended or could be considered based on guidelines from the American College of Gastroenterology. Indications for screening included men or women with chronic symptoms (greater than 5 years) of gastroesophageal reflux disease (GERD) and two or more risk factors for Barrett's esophagus or esophageal adenocarcinoma: Caucasian race, age ≥50 years, chronic GERD symptoms, current or prior history of smoking, central obesity as defined as a waist circumference greater than 88 centimeters, waist to hip ratio greater than 0.8, family history of Barrett's esophagus or family history of esophageal adenocarcinoma[10]. Patients were enrolled prospectively and consent to participate was obtained voluntarily for each patient. Based on clinical evaluation, individuals were assigned either to the Barrett's group or the GERD without Barrett's group.

Clinical Characteristics. Following endoscopy, physical examination and scripted interviews, the presence of Barrett's esophagus, age, gender, body mass index (BMI), ethnicity, presence of a hiatal hernia, smoking history and use/dose of proton pump inhibitors were recorded. For patients with Barrett's esophagus, the presence of dysplasia and the length of the Barrett's column were also recorded.

Endoscopy. Prior to its use, the endoscope was sterilized and placed in a sterile container. The endoscope was then inserted into the esophagus and advanced to the gastroesophageal junction without entering the stomach. The endoscope was then removed from the patient and swabbed while ensuring it did not contact any other surfaces. The endoscope was then re-inserted and the full examination was completed. During the endoscopy, biopsies of the esophagus were taken from 1) the proximal third of the esophagus and 2) distal esophagus, within 3 centimeters of the gastroesophageal junction. A swab of the uvula was also obtained using a sterile swab and immediately before the endoscopy was begun.

DNA extraction. Once obtained during endoscopy, tissue biopsies were placed into sterile Powerbead tubes pre-loaded with 0.1 mm glass beads (Qiagen, Germantown, MD) plus external lysis buffer in vitro diagnostic (200 μL, Roche Applied Science, Indianapolis, IN). Tissues were homogenized at 30 Hz for 5 minutes using a Tissuelyser I I homogenizer (Qiagen). Swabs from the uvula were placed into sterile PBS, vortexed and then were aliquoted 1:1 into the external lysis buffer (100 μL). Sample lysates were deposited into individual wells of 96 deep-well processing plates. DNA was subsequently extracted in high-throughput fashion using a MagNA Pure 96 instrument running a DNA and viral small volume-in vitro diagnostic extraction kit according to the manufacturer's protocol (Roche). After extraction, a portion of the DNA was evaluated by Ion Torrent Next Generation Sequencing or using the EMB. The remaining material was archived at −20 C.

Ion Torrent Next Generation Sequencing. Sample sequencing was carried out using a fusion-PCR method. Briefly, fusion-primers were designed in accordance with the manufacturer's guidelines (Ion Amplification Library Preparation—Fusion Method, Life Technologies, Carlsbad, CA) using Ion Xpress Barcodes linked to 16S gene primer pairs targeting hyper-variable regions 1-8[11]. Each 25 μl PCR was carried out using: 12.5 μl iQ Supermix™ (Bio-Rad, Hercules, CA), 1 μl of both forward and reverse (5 μM) primers, 9.5 μl nuclease-free water and 1 μl of DNA template. A total of 3 biopools of DNA created by equimolar mixing of the first 5 patient samples were analyzed. Each biopool represented DNA from the uvula swab, the proximal esophageal mucosal tissue or the distal esophageal mucosal tissue. The DNA biopools were then used as templates for creation of subsequent fusion 16s libraries. PCR was completed in a c1000 thermocycler (Bio-Rad) using the following parameters: Cycle 1), 95 C, 3 minutes, Cycle 2), Step 1: 95 C, 45 seconds; Step 2: Primer-specific annealing temps., 45 seconds; Step 3: 72 C, 2 minutes, repeat 39×; Step 4: 72 C, 7 minutes. PCR products were purified using Qiagen Qiaquick spin-columns and quantified using a spectrophotometer (Bio-Rad). PCR products were then diluted, mixed in equal proportion and sequenced on an Ion Torrent GeneStudio S5 System using Ion 520 sequencing kits together with 520 size chips following the manufacturer's instructions (Life Technologies).

Bioinformatics for Ion Torrent. After generation, sequencing reads were filtered for quality and binned according to Ion Xpress barcode using Ion Torrent Suite software version 5.10.0. Sequencing reads in FASTQ format were further processed using web-based Galaxy software[12]. First, raw FASTQ files were normalized using the FASTQ groomer tool function. Next, each barcoded read was trimmed to remove the primer sequence and subsequently filtered to the expected size of the 16S gene target. After this level of processing, the sequence reads were concurrently compared to the SILVA 16S database using bowtie 2 software[13-14]. This yielded a call to species or genera level as well as the number of times each sequence matched the database (hit-rate). When multiple calls to a genus were made, the number of hits were added accordingly. These numbers were then converted to percentage of total to give an overall ratio of the sequenced sample.

qPCR Evaluation by Esophageal Microbiome Array (EMB). To construct the EMB, Ion Torrent data and information from the esophageal disease literature[15-22] were compiled to select the most commonly detected organisms from the uvula to the distal esophagus ultimately creating a list of 46 targets that collectively represented greater than 85 percent of the detected microbiota in the Ion Torrent sequencing datasets. Two control qPCR targets were added to address the human DNA (hGAPDH) and total bacterial genomic loads (total 16S) creating a 48 target panel that was constructed in a skirted 96-well plate format (ThermoFisher Scientific Inc.). The 48 target array was constructed in 6×8 format allowing for evaluation of 2 samples per 96 well plate (FIG. 1). Each 25 μl PCR was carried out using: 12.5 μl iQ SYBR green Supermix™ (Bio-Rad), 1 μl of each forward and reverse (5-10 μM) primer, 9.5 μl nuclease-free water and 1 μl of DNA template. qPCR was completed in a c1000 thermocycler equipped with a CFX™ reaction module (Bio-Rad) using the following parameters: Cycle 1), 95 C, 3 minutes, Cycle 2), Step 1: 95 C, 30 seconds, Step 2: annealing 60 C, 30 seconds, extension 72 C, 30 seconds repeat 39×, Step 3: 72 C, 2 minutes, Step 4: Melt-curve 75 C-89 C, 0.2 C temperature increments with 5 second plate read time. Fluorescent signal data were collected at the end of each annealing/extension step. Starting quantity values were extrapolated from standard curves of plasmids harboring the PCR targets previously confirmed by Sanger sequencing. Any organism that was below the limit of detection was categorized as not detected. Mathematical analyses were performed using Excel™ (Microsoft Corp., Redmond, WA).

Plasmid dilution verification of limit of detection. To determine the limit of detection for each organism in the array, an equal concentration of plasmids representing cloned PCR targets on the EMB array were mixed in a 1:1 ratio. This mixture was 10-fold serially diluted from 10e7 to 10 copies. Five replicate EMB arrays were used for each concentration of the plasmid mix including $10^7$, $10^5$, $10^3$, $10^2$ and 10. The results were used to establish a dynamic range for quantification as well as the lower limit of detection for each PCR target under the EMB qPCR thermocycling conditions.

Quantitative PCT (qPCR). The various organisms can be detected using, e.g., qPCR. qPCR is a well-established method for the detection, quantification, and typing of different microbes in clinical samples. Exemplary qPCR methods for use with the present invention include: (1) non-specific fluorescent dye intercalation with any double-stranded DNA and/or (2) sequence-specific oligonucleotides DNA probes that are labelled with a fluorescent reporter, which permits detection only after hybridization of the probe with its complementary sequence.

Figure 3:
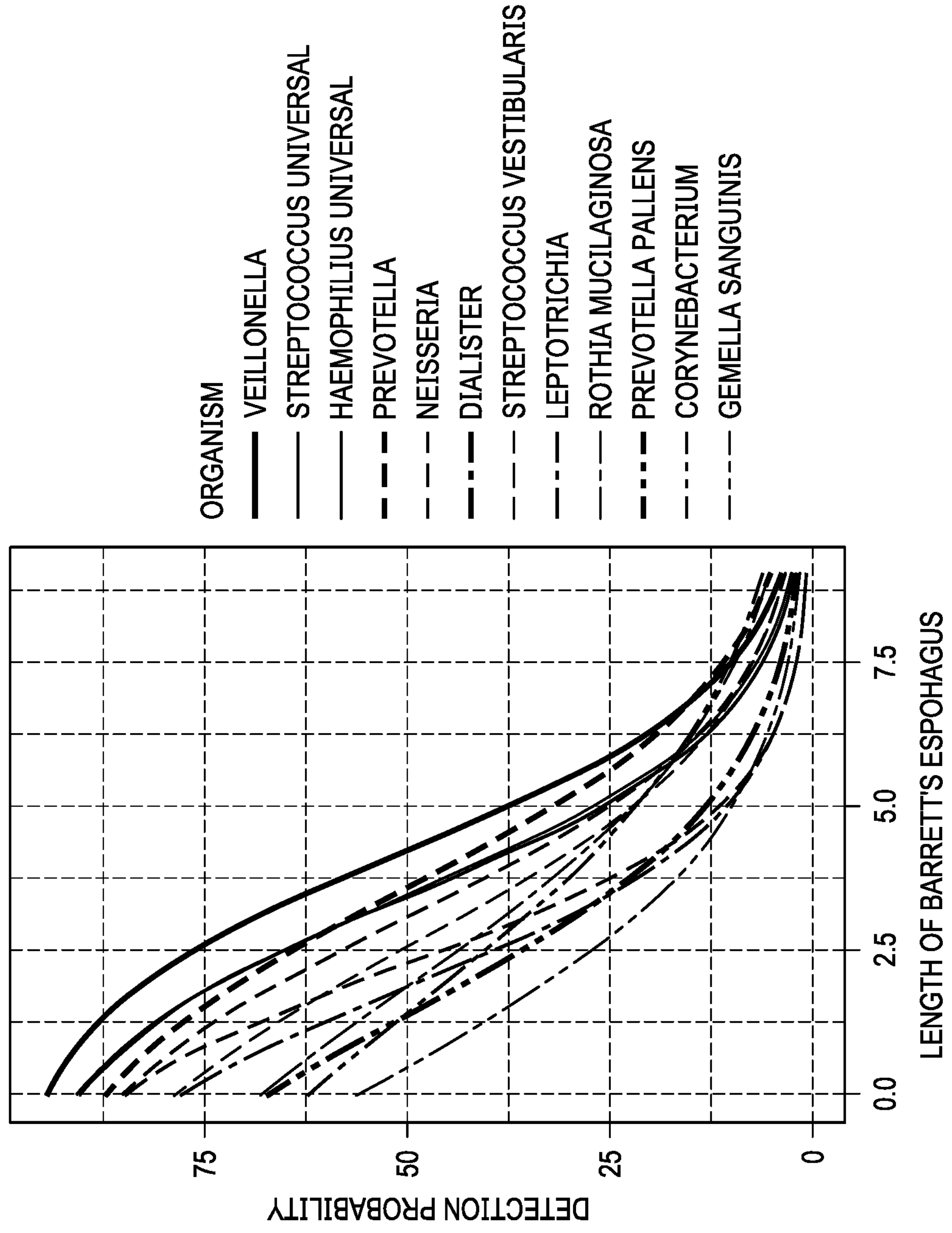
FIG. 3 shows organisms with detection rates which correlated with length of Barrett's column.
Figure 4:
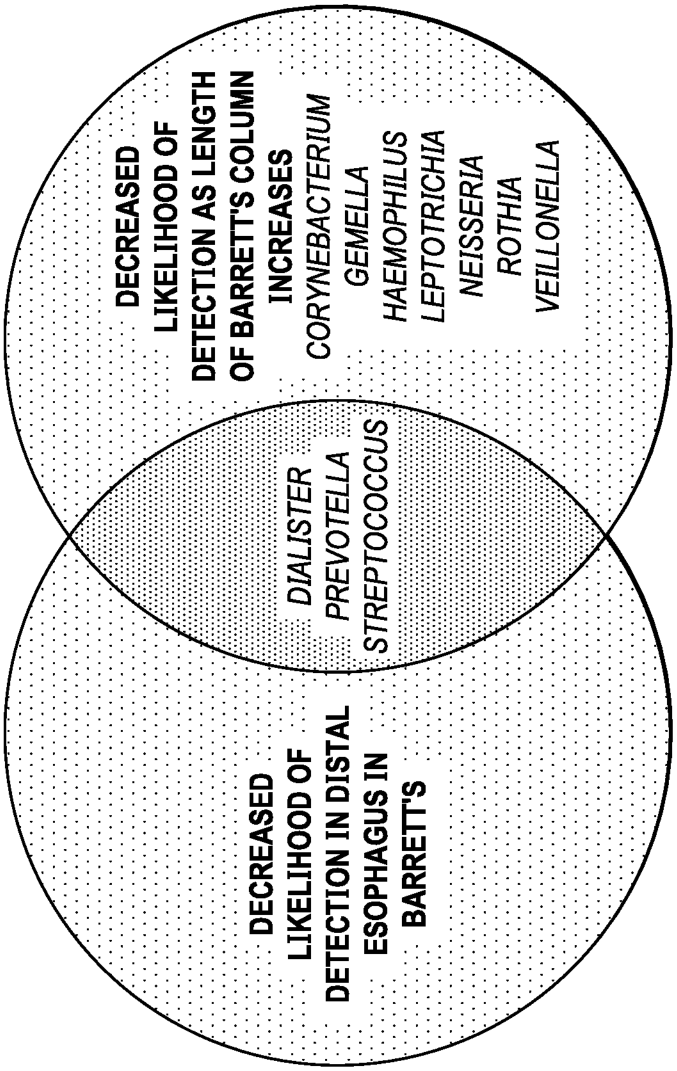
FIG. 4 is a Venn diagram showing genera significantly related to presence/absence of Barrett's esophagus and length of Barrett's column.
Figure 5A:
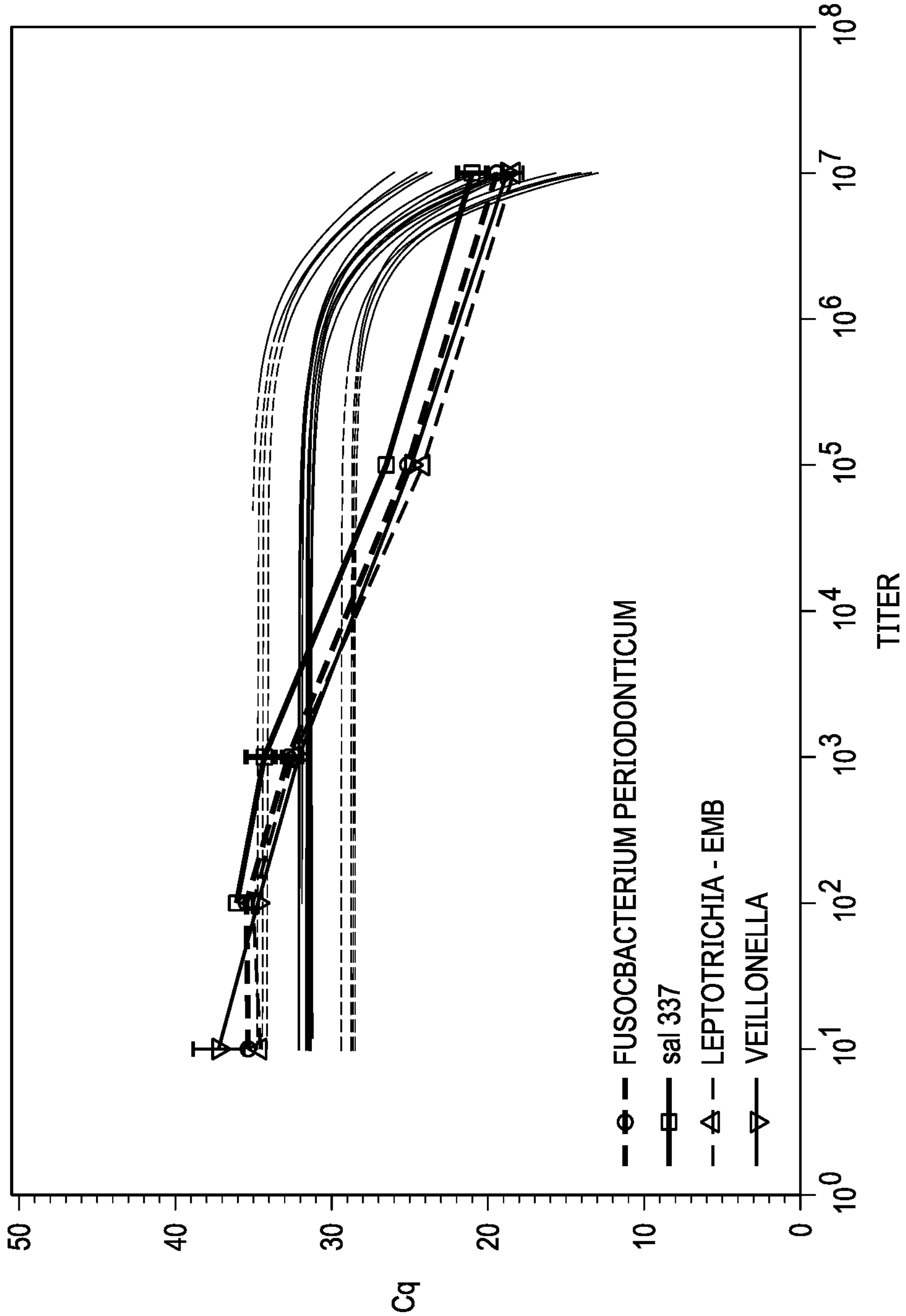
FIGS. 5A-5E are graphs that show the limit of detection of the EMB targets.
Figure 5B:
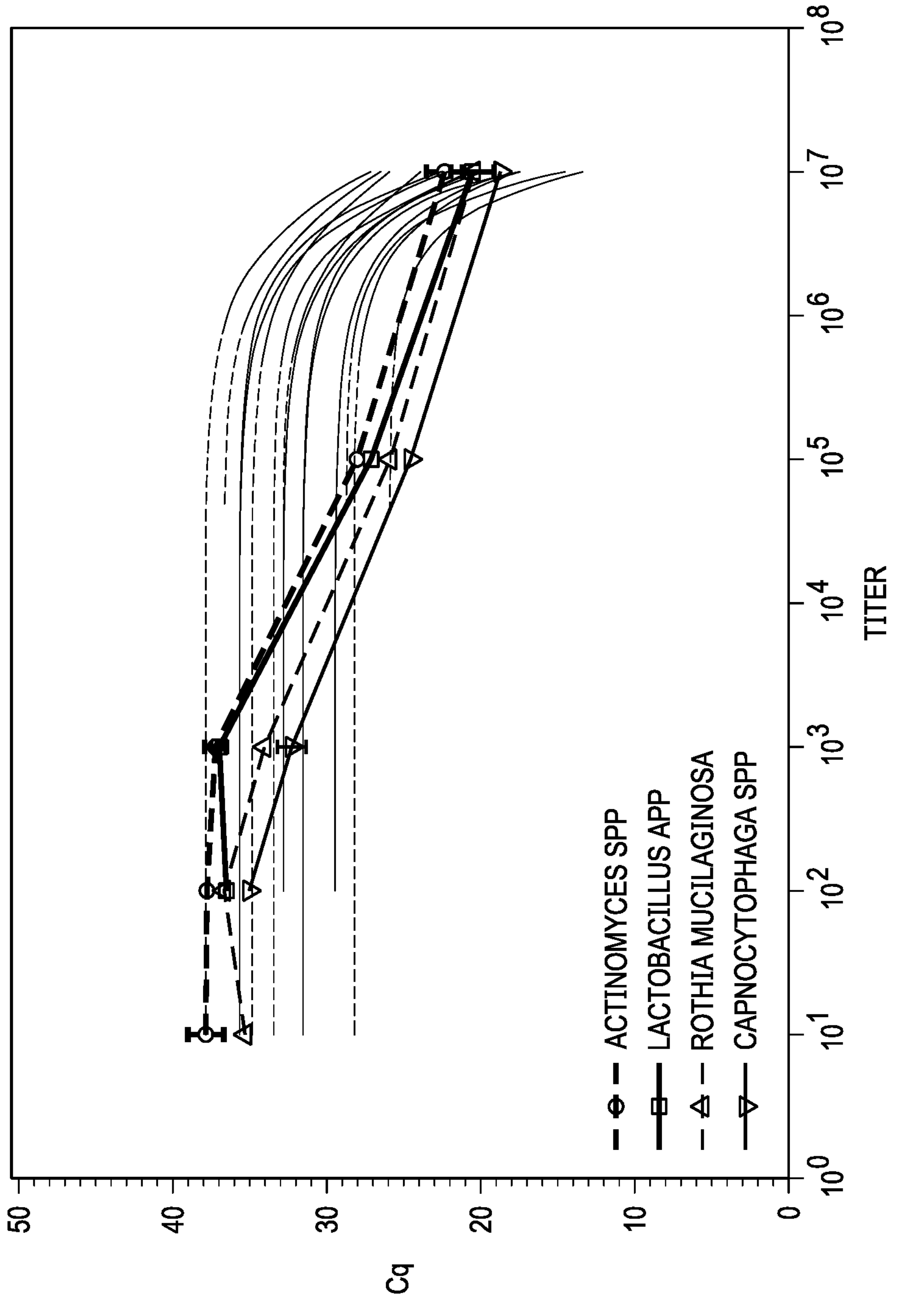
Figure 5C:
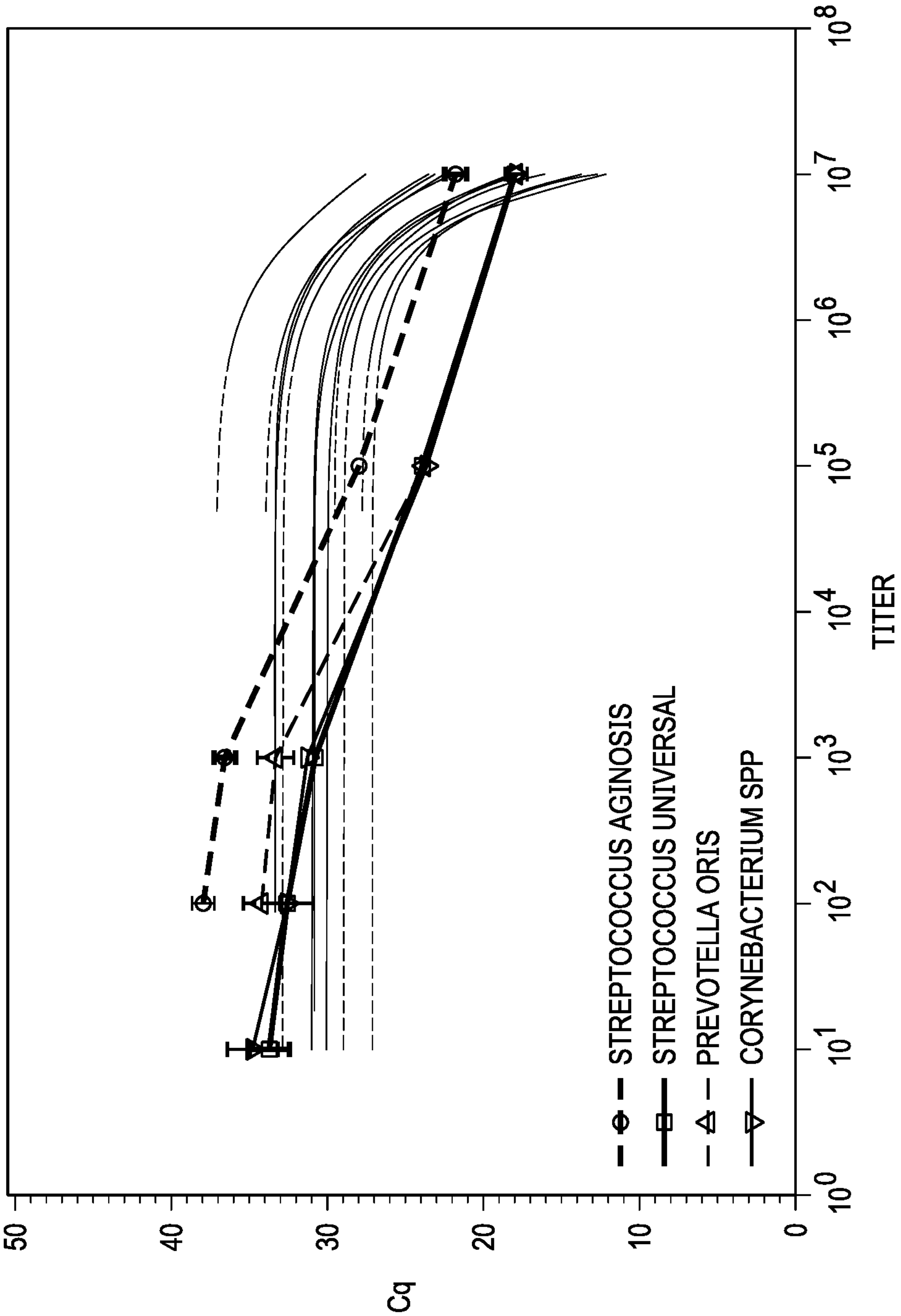
Figure 5D:
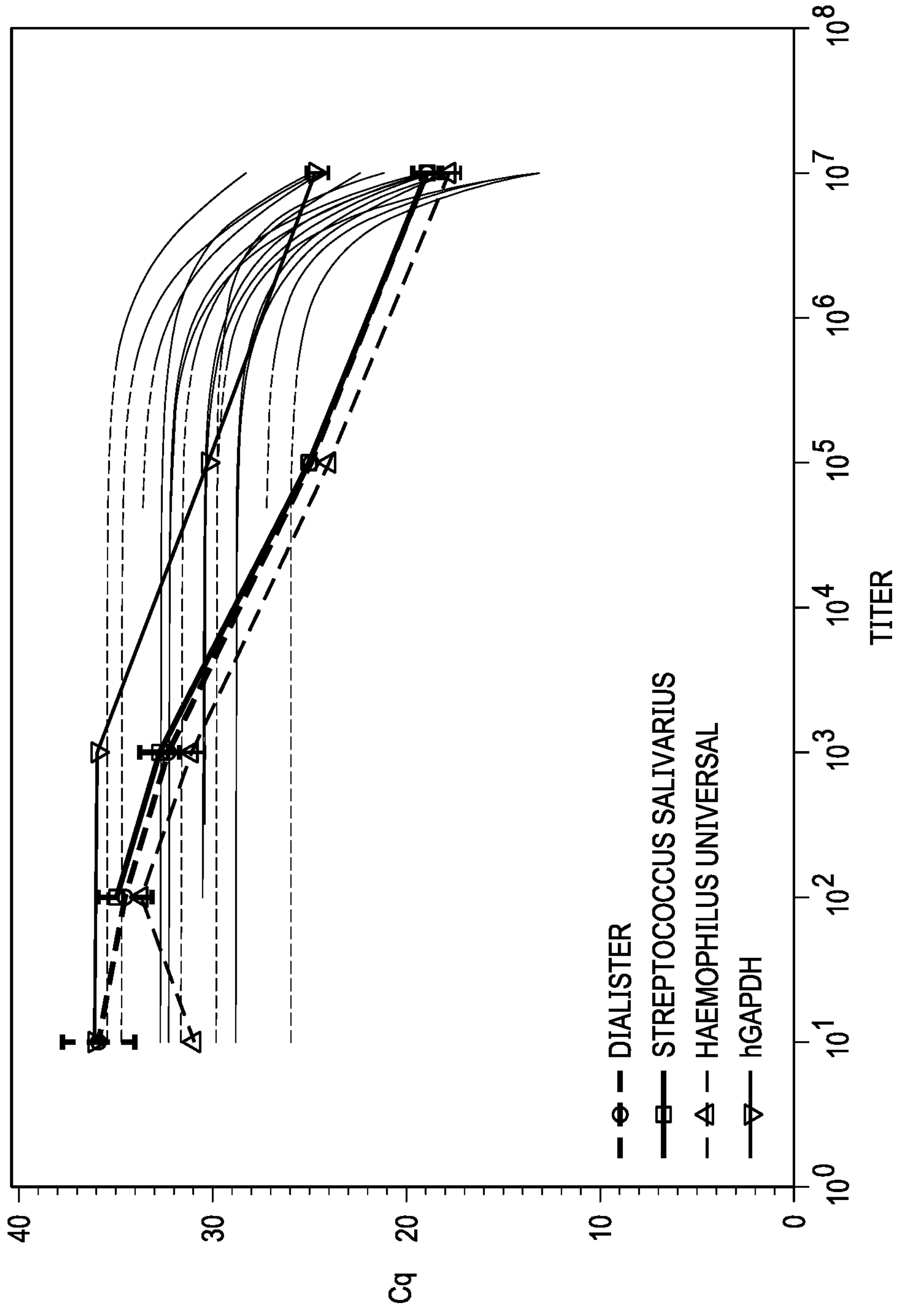
Figure 5E:
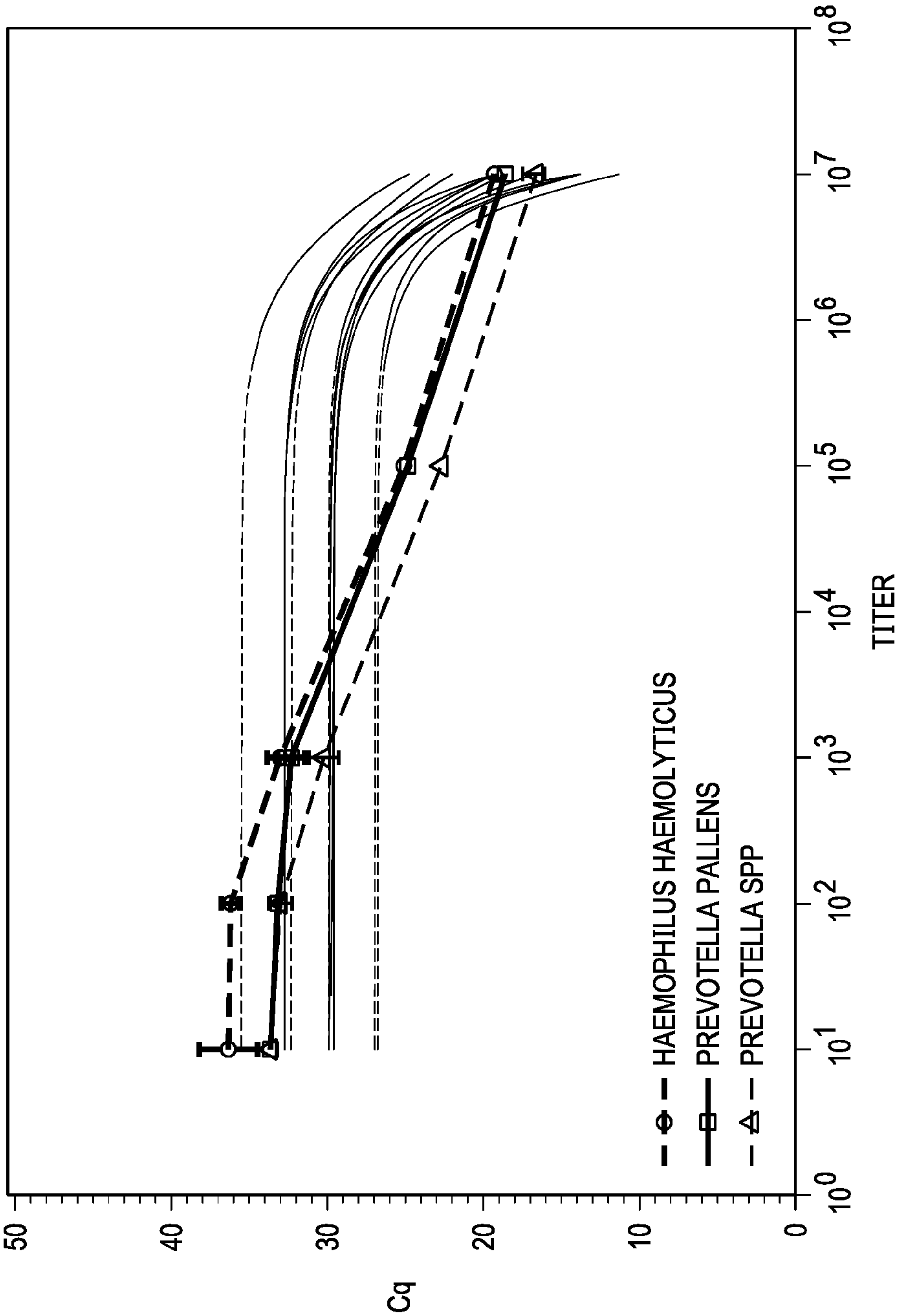

Statistical analysis. The detection or non-detection of each organism was recorded in every sample in every patient. 2-way Firth-penalized logistic regression was used to relate the detection status to a selected variable (e.g. Barrett's esophagus vs. GERD without Barrett's esophagus) separately for each organism at each location. 2-way Firth-penalized logistic regression was used instead of conventional logistic regression due to the extreme values of detection incidence near 0% or 100% in many cases. The graphs for each organism were likewise modeled per 2-way Firth-penalized logistic regression, relating detection status to an association between a group (e.g. Barrett's esophagus vs. GERD without Barrett's esophagus) and a location (uvula, proximal esophagus, distal esophagus). The graphs illustrate a model-predicted probability of detection at each location. To determine the association of the length of the Barrett's column with microbiota, Firth logistic regression was used for detection, restricted to the Barrett's esophagus group only, controlling for the covariates to determine the association between location and length of the Barrett's column. FIGS. 2-4 were drawn with predictions based on samples with no history of smoking and no esophagitis. Statistical analyses were performed using R statistical software (R Core Team, 2018, version 3.5.1). In all statistical tests, $\alpha=0.05$.

Demographics. A total of 74 total patients were enrolled in the study, including 34 patients in the Barrett's group and 40 patients in the GERD without Barrett's group. Demographic information for each patient is listed in Table 1. Demographic data was not available for the first 5 patients in the Barrett's group.

TABLE 1

Cohort Demographics

| ID | Group | Gender | Age | BMI | Hiatal hernia | Current smoker | Current PPI use | PPI dose |
|---|---|---|---|---|---|---|---|---|
| 1 | Barrett's | | | | | | | |
| 2 | Barrett's | | | | | | | |
| 3 | Barrett's | | | | | | | |
| 4 | Barrett's | | | | | | | |
| 5 | Barrett's | | | | | | | |
| 6 | Barrett's | M | 71 | 29.2 | N | N | Y | 80 |
| 7 | Barrett's | M | 40 | 43.0 | Y | Y | Y | 80 |
| 8 | Barrett's | F | 52 | 22.3 | N | N | Y | 80 |
| 9 | Barrett's | M | 62 | 24.0 | Y | N | Y | 40 |
| 10 | Barrett's | M | 54 | 38.1 | N | N | Y | 40 |
| 11 | Barrett's | M | 63 | 31.0 | Y | N | Y | 20 |
| 12 | Barrett's | M | 66 | 23.8 | Y | N | Y | 80 |
| 13 | Barrett's | M | 62 | 23.2 | N | N | Y | 20 |
| 14 | Barrett's | F | 67 | 37.3 | N | N | Y | 40 |
| 15 | Barrett's | M | 60 | 24.6 | Y | Y | Y | 40 |
| 16 | Barrett's | M | 56 | 29.9 | Y | Y | Y | 40 |
| 17 | Barrett's | F | 52 | 28.9 | N | Y | Y | 40 |
| 18 | Barrett's | F | 58 | 54.7 | Y | N | Y | 40 |
| 19 | Barrett's | M | 70 | 33.8 | N | N | Y | 20 |
| 20 | Barrett's | F | 77 | 31.3 | N | N | Y | 80 |
| 21 | Barrett's | F | 64 | 44.0 | N | N | Y | 40 |
| 22 | Barrett's | F | 68 | 29.6 | Y | N | N | 0 |
| 23 | Barrett's | M | 56 | 52.6 | Y | P | Y | 80 |

TABLE 1-continued

Cohort Demographics

| ID | Group | Gender | Age | BMI | Hiatal hernia | Current smoker | Current PPI use | PPI dose |
|---|---|---|---|---|---|---|---|---|
| 24 | Barrett's | F | 41 | 22.8 | Y | N | Y | 80 |
| 25 | Barrett's | M | 75 | 27.5 | N | N | Y | 40 |
| 26 | Barrett's | M | 73 | 33.6 | Y | N | Y | 40 |
| 27 | Barrett's | M | 73 | 26.9 | N | N | Y | 40 |
| 28 | Barrett's | F | 62 | 31.1 | Y | N | Y | 20 |
| 29 | Barrett's | F | 62 | 29.2 | N | N | Y | 40 |
| 30 | Barrett's | F | 76 | 17.9 | N | Y | Y | 20 |
| 31 | Barrett's | M | 37 | 25.8 | Y | N | Y | 60 |
| 32 | Barrett's | M | 68 | 26.7 | N | Y | Y | 40 |
| 33 | Barrett's | M | 58 | 40.4 | Y | N | Y | 80 |
| 34 | Barrett's | M | 71 | 29.2 | Y | N | Y | 20 |
| 35 | GERD without Barrett's | F | 53 | 23.4 | N | N | N | 0 |
| 36 | GERD without Barrett's | F | 47 | 28.0 | Y | Y | Y | 40 |
| 37 | GERD without Barrett's | M | 43 | 22.0 | Y | N | Y | 40 |
| 38 | GERD without Barrett's | M | 63 | 27.1 | N | N | Y | 80 |
| 39 | GERD without Barrett's | F | 66 | 31.4 | Y | N | Y | 40 |
| 40 | GERD without Barrett's | F | 50 | 36.3 | N | N | Y | 20 |
| 41 | GERD without Barrett's | F | 43 | 37.1 | N | N | Y | 80 |
| 42 | GERD without Barrett's | M | 49 | 27.6 | Y | N | Y | 40 |
| 43 | GERD without Barrett's | M | 58 | 30.1 | N | N | Y | 40 |
| 44 | GERD without Barrett's | M | 54 | 33.8 | N | Y | Y | 80 |
| 45 | GERD without Barrett's | F | 49 | 24.4 | N | N | Y | 40 |
| 46 | GERD without Barrett's | F | 62 | 34.4 | Y | Y | N | 0 |
| 47 | GERD without Barrett's | M | 51 | 33.3 | Y | N | Y | 40 |
| 48 | GERD without Barrett's | M | 60 | 30.8 | N | N | Y | 80 |
| 49 | GERD without Barrett's | F | 55 | 35.5 | Y | N | Y | 40 |
| 50 | GERD without Barrett's | F | 55 | 40.3 | N | N | Y | 40 |
| 51 | GERD without Barrett's | M | 67 | 29.9 | N | N | Y | 40 |
| 52 | GERD without Barrett's | M | 62 | 21.1 | N | Y | N | 0 |
| 53 | GERD without Barrett's | F | 66 | 34.9 | N | N | Y | 40 |
| 54 | GERD without Barrett's | M | 66 | 28.5 | N | N | Y | 40 |
| 55 | GERD without Barrett's | M | 69 | 23.9 | N | N | Y | 20 |
| 56 | GERD without Barrett's | M | 63 | 30.4 | N | N | Y | 40 |
| 57 | GERD without Barrett's | F | 67 | 39.1 | N | N | Y | 40 |
| 58 | GERD without Barrett's | F | 63 | 33.3 | Y | N | Y | 40 |
| 59 | GERD without Barrett's | F | 63 | 26.2 | N | N | Y | 40 |
| 60 | GERD without Barrett's | F | 68 | 33.7 | Y | N | Y | 40 |
| 61 | GERD without Barrett's | M | 68 | 38.8 | Y | N | Y | 80 |
| 62 | GERD without Barrett's | F | 71 | 25.7 | Y | Y | Y | 40 |
| 63 | GERD without Barrett's | M | 50 | 26.6 | N | N | Y | 20 |
| 64 | GERD without Barrett's | M | 56 | 31.6 | Y | Y | Y | 20 |
| 65 | GERD without Barrett's | M | 66 | 26.0 | N | N | Y | 40 |
| 66 | GERD without Barrett's | F | 52 | 38.6 | N | N | N | 0 |
| 67 | GERD without Barrett's | F | 64 | 38.5 | N | N | Y | 40 |
| 68 | GERD without Barrett's | M | 83 | 25.2 | Y | N | Y | 40 |
| 69 | GERD without Barrett's | M | 54 | 27.3 | N | Y | Y | 40 |
| 70 | GERD without Barrett's | M | 50 | 30.7 | N | N | Y | 40 |
| 71 | GERD without Barrett's | F | 76 | 28.3 | N | N | Y | 40 |
| 72 | GERD without Barrett's | M | 63 | 36.4 | N | N | N | 0 |
| 73 | GERD without Barrett's | F | 62 | 39.3 | N | Y | Y | 40 |
| 74 | GERD without Barrett's | F | 66 | 37.5 | N | N | N | 0 |

The average age in the entire cohort was 60.2 years. The majority of patients were currently on proton pump inhibitor therapy at the time of endoscopy, including 96% of the Barrett's group and 85% of the GERD without Barrett's group. When comparing the Barrett's group to the GERD without Barrett's group, there were no significant differences in age, gender ratio, BMI, tobacco use, presence of a hiatal hernia, current use of proton pump inhibitors or dose of proton pump inhibitors (Table 2).

Microbiota Detection Patterns in Patients With and Without Barrett's Esophagus. There were statistically significant differences in the likelihood of detection of multiple organisms in the Barrett's group compared to the GERD without Barrett's group. There were significant differences in likelihood of detection in 1 species (*Streptococcus mutans*) at the uvula, 2 genera or species (*Actinomyces, Prevotella pallens*) at the proximal esophagus and 4 genera or species (*Dialister, Prevotella* unspecified, *Streptococcus salivarius, Streptococcus* unspecified) at the distal esophagus (FIG. 2). Demographic data was unavailable in 5 patients in the Barrett's esophagus group.

TABLE 2

Comparison of Study Groups*

| | Barrett's esophagus | Non-Barrett's esophagus | p-value |
|---|---|---|---|
| N | 34 | 40 | |
| Male | 62% (18/29) | 50% (20/40) | 0.32 |
| Age, years (mean) | 61.7 ± 10.7 | 59.0 ± 8.9 | 0.26 |
| BMI (mean) | 31.5 ± 8.7 | 31.1 ± 5.5 | 0.83 |
| Hiatal hernia | 52% (15/29) | 35% (14/40) | 0.16 |
| Current smoker | 24% (7/29) | 20% (8/40) | 0.61 |
| Current use of proton pump inhibitors | 97% (28/29) | 85% (34/40) | 0.23 |

TABLE 2-continued

| Comparison of Study Groups* | | | |
|---|---|---|---|
| | Barrett's esophagus | Non-Barrett's esophagus | p-value |
| Dose of proton pump inhibitors (milligrams) | 46.2 | 22.0 | 0.11 |
| Presence of dysplasia | 7% (2/29) | N/A | |
| Length of Barrett's, centimeters (mean) | 3.0 ± 2.7 | N/A | |

Severity of Barrett's Esophagus Versus Microbiome Pattern. Among patients with Barrett's esophagus, the severity of disease was measured by measuring the length of the column of Barrett's esophagus (Barrett's column). There was a decreased likelihood of detection of multiple organisms as the length of the Barrett's column increased. In particular, 10 different genera (*Corynebacterium, Dialister, Gemella, Haemophilus, Leptotrichia, Neisseria, Prevotella, Rothia, Streptococcus, Veillonella*) on the EMB array had a significantly decreased likelihood of detection as the length of the Barrett's column increased (FIG. 3). This relationship between Barrett's length and detection existed only at the distal esophagus. There was no correlation between Barrett's length and detection of any organism at the proximal esophagus or the uvula.

Finally, there was an overlap in organisms that were significantly associated with the presence or absence of Barrett's esophagus and the severity of Barrett's esophagus (FIG. 4).

Microbiome Detection Patterns based on Clinical Factors. No other demographic factors, such as age, gender, body-mass index, geographic location, smoking history or presence of hiatal hernia, were associated with differences in likelihood of detection.

Limit of detection (LOD) for each target within the array. The inventors established the LOD by testing a series of 10-fold dilutions of an equal concentration mix of plasmids containing each PCR target within the range of $10^7$ to 10 copies. Five replicate EMB arrays were completed for each concentration establishing a dynamic range for quantification for each PCR target under the EMB qPCR thermocycling conditions. The results indicated that the LOD ranged from. <100 to 700 copies of a specific target per tissue or swab sample (Table 3).

TABLE 3

LOD by testing a series of 10-fold dilutions of an equal concentration mix of plasmids containing each PCR target within the range of $10^7$ to 10 copies

| EMB Target | Estimated LOD (copies) |
|---|---|
| *Actinomyces* | <10 |
| *Campylobacter showae* | 50 |
| *Campylobacter* | 50 |
| *Capnocytophaga* | 50 |
| *Corynebacterium* | 20 |
| *Dialister* | <10 |
| *Fusobacterium periodonticum* | 25 |
| *Gemella sanguinis* | 70 |
| *Gemella* spp | 70 |
| *Haemophilus haemolyticus* | 10 |
| *Haemophilus parainfluenzae* | 70 |
| *Haemophilus* | 50 |
| *Leptotrichia* | 25 |
| *Leptotrichia wadei* | 50 |

TABLE 3-continued

LOD by testing a series of 10-fold dilutions of an equal concentration mix of plasmids containing each PCR target within the range of $10^7$ to 10 copies

| EMB Target | Estimated LOD (copies) |
|---|---|
| *Neisseria* | 40 |
| *Porphyromonas endodontalis* | 25 |
| *Prevotella melaninogenica* | 50 |
| *Prevotella nigrescens* | 30 |
| *Prevotella oris* | 40 |
| *Prevotella pallens* | 30 |
| *Prevotella* | 20 |
| *Rothia mucilaginosa* | 60 |
| *Rothia* | 50 |
| Sal 337 (uncultured salivary isolate) | 50 |
| *Streptococcus pneumoniae* | 30 |
| *Streptococcus salivarius* | 50 |
| *Streptococcus* | <10 |
| *Veillonella* | 20 |

FIGS. 5A-5E are graphs that show the limit of detection of the EMB targets. FIG. 6 is a table with the results for the limit of detection of the various bacteria.

Finding effective screening strategies for solid tumors can be challenging. The main gap in implementing a successful screening plan for esophageal cancer is the relatively low incidence of disease in patients with the known risk factors. Although Barrett's esophagus is a known risk factor for esophageal cancer, only 0.1% of patients with Barrett's esophagus develop malignancy. This low incidence for one of the major risk factors highlights the current gap in clinical care that exists for esophageal cancer. This fact highlights the critical need to better stratify the risk of getting esophageal cancer among patients with Barrett's esophagus as well as the need to identify additional risk factors that have a higher association with incidence of esophageal cancer.

Evaluation of the microbiota on this mucosa is a potential solution to address this gap in clinical care[23-25]. As such, the inventors determined if there was a microbiota pattern that was associated with Barrett's esophagus. The rationale was that a "Barrett's microbiome" may be able to predict which patients are at risk of developing Barrett's esophagus, even if they have not yet manifested histologic changes. By the same reasoning, a high-risk microbiome may be able to predict which patients would be most likely to develop esophageal cancer in the future. With this information, screening programs could be tailored more effectively, and a cohort with higher risk could be identified. And the nature of the screening endoscopy could be changed. Currently the endoscopy focuses on the presence or absence of Barrett's esophagus, the length of the Barrett's column and the presence or absence of dysplasia. In the future, other information from the screening endoscopy could include the presence or absence of a high-risk community of microbiota[26-27]. Finally, if relevant organisms can be associated with an increased risk of disease, then other modalities beside endoscopy could be used. In the future a breath or saliva test may be possible, which would allow for a higher percentage of at-risk patients to be screened at reduced cost and procedure-related risk.

First, it showed that there was a microbiota community structure that associated with the presence of Barrett's esophagus. Unlike prior studies, the present study using an array showed detection differences only for the presence or absence of Barrett's esophagus, and not for other factors described in other studies such as age, gender or presence of hiatal hernia[28-31]. The systematic methodology employed to create the customized EMB array helped to make it an appropriate investigative tool to discern a high-risk community of microbiota. The current data with the 74 patient cohort also identified organisms on the EMB array that are of little consequence to that clinical question. Importantly, the EMB array offered greater utility than traditional next generation sequencing with a much higher sensitivity than that reported for next generation sequencing datasets (Supplemental table 1) as well as true quantitation not possible with 16S next generation sequencing.

Second, this study showed that as the severity of Barrett's esophagus increased the likelihood of detection of multiple organisms decreased, and that this decreased likelihood was localized to the distal esophagus. This finding is novel and has not been described in previous literature. Because the length of the Barrett's column correlates with the likelihood of developing cancer, these organisms may also be decreased or absent in patients who ultimately develop esophageal cancer. The use of 16S next generation sequencing for this purpose would likely fail to detect many of these low abundance genera or species. The EMB approach and the data produced in this study demonstrate that there are multiple organisms that are protective alone or in combination against the development of Barrett's esophagus and, by extension, esophageal cancer.

Although it is possible that the environmental changes in the distal esophagus that cause Barrett's esophagus also allow for certain microbes to flourish, there is a distinct possibility that there is a mechanism by which certain organisms act to prevent esophageal disease. It is now possible to determine which organisms can interact with the distal esophageal environment to cause or prevent Barrett's esophagus. By way of explanation, and in no way a limitation of the present invention, it is likely that at least some of the same interactions will explain the conversion of normal esophagus to Barrett's esophagus as well as to esophageal cancer. The acidic nature of the intraluminal milieu is a unique characteristic of the distal esophagus that may impact the microbiome at this location.

In this study, a screening group who were evaluated by endoscopy and found to have GERD without Barrett's as a control. This meant the added risk of mucosal biopsy for these research purposes was minimal but, more importantly, the controls all had symptoms of GERD. This control group was selected because it would also have a rather acidic intraluminal environment in the distal esophagus. Although pH testing was not performed in study, it is known that risk of Barrett's esophagus increases as the absolute amount of acid exposure increases. As regards the intraluminal environment, factors such as motility, may also affect the risk of development of Barrett's esophagus.

Barrett's esophagus is a risk factor for esophageal cancer. Unfortunately, it is a relatively crude risk factor as only 1 in 860 people with Barrett's esophagus ultimately develop esophageal cancer. These studies and the analysis thereof have now shown that there is a group of organisms that correlate with Barrett's esophagus. Furthermore, the levels of these organisms appear to correlate with the severity of Barrett's esophagus. Identification of these organisms can now be used to treat Barrett's esophagus at an earlier timepoint.

The present invention can also be used to stratify risk and guide treatment in patients with Barrett's esophagus. A kit that detects the various bacteria, such as that shown in FIG. 1, can be used onto which a mucosal biopsy, via EGD, or a salivary specimen from a swab, is analyzed for the presence and levels of these organisms. Based on the results, one or more treat treatment strategies can be selected, as discussed below.

Based on this new understanding of Barrett's esophagus, it is now possible to manipulate the esophageal microbiome to be more protective against development of disease or prevent an increase in disease severity (e.g., length of Barrett's column) as it progresses toward esophageal cancer. Treatments for use with the present invention include probiotics that increase beneficial bacteria and/or decrease bacterial associated with Barrett's esophagus. The treatment also includes the use of one or more chemopreventive agent(s) that alter the microbiome toward a more favorable one. Though previous literature has also identified a microbiome pattern which differs in patients with Barrett's esophagus compared to patients without Barrett's esophagus, the present study used a detection/non-detection analysis. Other studies have employed a "shotgun" approach, in which a much wider array of organisms is used, and diversity indices were reported as differing between the different groups being studied.

Using the present invention, if the results of the kit determined that the patient was at very high risk for esophageal cancer, a potential treatment would be endoscopic mucosal resection of the distal esophagus. This procedure is performed during endoscopy and would remove the inner lining of the distal esophagus, where esophageal cancer forms in the majority of patients. There is some risk and morbidity to this procedure, so it is not justified now in all patients with Barrett's esophagus given that the risk of developing cancer is only approximately 0.1% as above.

If endoscopic mucosal resection was not possible or revealed that an in situ esophageal cancer was already present, then an esophagectomy would be the recommended treatment. The benefit of this strategy is that the 5-year survival from this treatment plan would be close to 100% since the cancer would have been discovered at a very early stage. Currently, the 5-year survival for esophageal cancer is only 19%.

By contrast, if the results of the kit showed moderate risk for esophageal cancer, an initial treatment strategy is increased surveillance. Usual surveillance strategy for Barrett's esophagus varies based on a number of factors, but it is common for many institutions to perform surveillance endoscopy once every 3 years. With a moderate risk based on this kit, an endoscopy (or even a salivary or breath sample) can be performed every 3 to 6 months.

If the results of the kit showed very low risk for esophageal cancer, then surveillance could potentially be eliminated completely. This would save a patient from the low but non-zero risk from the endoscopy and lead to more efficient and cost-effective surveillance of this disease process for the population.

The present invention provides a superior screening method that can be used to detect/non-detect relevant bacteria. Many of the organisms that were shown to be decreased in the Barrett's group have been seen in other studies as well. Organisms such as *Streptococcus, Prevotella* and *Veillonella* have been identified as being decreased in other studies[34-36], but these other studies largely studied the microbiome at the genera level and evaluated the relative abundance of organisms versus the detection/non-detection technique of the present invention. While species-level information may be important, the present invention showed that some species within the same genera did or did not correlate with the severity of disease. As an example,

*Streptococcus vestibularis* seemed to correlate with the severity of Barrett's esophagus while *Streptococcus sanguinis* did not.

In one embodiment, the present invention includes a method of detecting and treating a patient suspected of having Barrett's esophagus comprising, consisting essentially of, or consisting of: obtaining a biological sample from an esophagus of the patient; determining a microbiome in the biological sample by detecting the presence of bacteria by plasmid dilution verification or quantitative polymerase chain reaction (qPCR); wherein if the patient has a microbiome indicative of an increased risk of esophageal cancer treating the patient with at least one of: removing at least part of the esophagus, esophagectomy, probiotic therapy, chemically targeting elimination of bacteria indicative of an increased risk of esophageal cancer or increasing the frequency of endoscopic surveillance. In one aspect, the absence of *Streptococcus salivarius, Actinomyces, Prevotella*, or *Dialister* is indicative of an increased risk of esophageal cancer. In another aspect, the absence of *Corynebacterium, Dialister, Gemella, Haemophilus, Leptotrichia, Neisseria, Prevotella, Rothia, Streptococcus, Veillonella* is indicative of worsened severity of Barrett's esophagus and an increased risk of esophageal cancer. In another aspect, the method further comprises stratifying patients based on the presence of bacteria in the uvula, proximal esophagus and distal esophagus. In another aspect, the biological sample is an esophageal swab and mucosal biopsies were obtained from the uvula, proximal esophagus and distal esophagus. In another aspect, a decrease in *Streptococcus vestibularis* is indicative of Barrett's esophagus. In another aspect, the detection of *Streptococcus mutans* at the uvula is indicative of Barrett's esophagus. In another aspect, the lack of detection of *Actinomyces*, and *Prevotella pallens* at the proximal esophagus is indicative of Barrett's esophagus. In another aspect, the lack of detection of *Dialister, Prevotella* unspecified, *Streptococcus salivarius, Streptococcus* unspecified at the distal esophagus is indicative of Barrett's esophagus. In another aspect, the biological sample is obtained from the distal esophagus and a length of a Barrett's column correlated with a level of Barrett's esophagus leading to esophageal cancer. In another aspect, the biological sample is a breath sample, a saliva sample, or a biopsy of the esophagus. In another aspect, the presence of Barrett's esophagus is determined without use of age, gender or presence of hiatal hernia as a factor or factors.

In one embodiment, the present invention includes a method of detecting and treating a patient suspected of having Barrett's esophagus by plasmid dilution verification or quantitative polymerase chain reaction (qPCR) comprising, consisting essentially of, or consisting of: obtaining one or more samples from one or more locations of an esophagus of the patient; extracting RNA from the one or more sample; performing an amplification reaction to obtain amplification products of the extracted RNA; analyzing the amplification products and comparing to a known, available database containing sequencing of each of the one or more microorganisms to determine which microorganisms are detected and at what quantities when compared to a standard having a known amount of an extracted RNA. In one aspect, the RNA is extracted with a lysis buffer, a homogenizer, or both. In another aspect, the RNA is reverse transcribed into DNA before the addition of the fusion primers. In another aspect, the method further comprises the steps for plasmid dilution verification of adding fusion primers linked to hyper-variable regions for one or more target microorganisms in the extracted RNA; mixing an equal concentration of plasmids of cloned targets on an array of microorganisms with the sample in a 1:5 to 5:1 ratio between the extracting and adding steps. In another aspect, the ratio is 4:1, 3:1, 2:1, 1:1, 1:2, 1:3, or 1:4. In another aspect, the sample and the plasmids are serially diluted from $10^7$ to 10 copies. In another aspect, the method further comprises establishing a dynamic range for quantification and a lower-limit-of-detection for each cloned target, wherein the amplification is a quantitative polymerase chain reaction (qPCR) and the amplification is by thermocycling.

In one embodiment, the present invention includes a method of determining an extent of disease progression in a patient suspected of having Barrett's esophagus comprising, consisting essentially of, or consisting of: obtaining a biological sample from one or more locations of an esophagus of the patient; determining a microbiome in the biological sample by detecting the presence of bacteria by plasmid dilution verification or quantitative polymerase chain reaction (qPCR) at the one or more locations of the esophagus of the patient; and matching the extent of Barrett's esophagus to disease progression by detecting the presence of microorganisms at the one or more locations of the esophagus that correlate with different levels of Barrett's esophagus disease progression; and if the patient has a microbiome indicative or early Barrett's esophagus disease then increasing a frequency of Barrett's esophagus disease surveillance from every 3 months to every three years in three-month increments; or if the patient has a microbiome indicative of advanced Barrett's esophagus treating the patient with at least one of: removing at least part of the esophagus, esophagectomy, probiotic therapy, chemically targeting elimination of bacteria indicative of an increased risk of esophageal cancer or increased frequency of endoscopic surveillance. In one aspect, the absence of *Streptococcus* salivarius, *Actinomyces, Prevotella*, or *Dialister* is indicative of an increased risk of esophageal cancer. In another aspect, the absence of *Corynebacterium, Dialister, Gemella, Haemophilus, Leptotrichia, Neisseria, Prevotella, Rothia, Streptococcus, Veillonella* is indicative of an increased severity of Barrett's esophagus. In another aspect, the method further comprises stratifying patients based on the presence of bacteria in the uvula, proximal esophagus and distal esophagus. In another aspect, the biological sample is an esophageal swab and mucosal biopsies were obtained from the uvula, proximal esophagus and distal esophagus. In another aspect, a decrease in *Streptococcus vestibularis* is indicative of Barrett's esophagus. In another aspect, the detection of *Streptococcus mutans* at the uvula is indicative of Barrett's esophagus. In another aspect, the lack of detection of *Actinomyces*, and *Prevotella pallens* at the proximal esophagus is indicative of Barrett's esophagus. In another aspect, the lack of detection of *Dialister, Prevotella* unspecified, *Streptococcus salivarius, Streptococcus* unspecified at the distal esophagus is indicative of Barrett's esophagus. In another aspect, the biological sample is obtained from the distal esophagus and a length of a Barrett's column correlated with a level of Barrett's esophagus leading to esophageal cancer. In another aspect, the biological sample is a breath sample, a saliva sample, a biopsy of the esophagus or a serum sample. In another aspect, the presence of Barrett's esophagus is determined without use of age, gender or presence of hiatal hernia as a factor or factors.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±0.1, 0.5, 1, 2, 3, 4, 5, 6, 7, 10, 12 or 15%, or as understood to be within a normal tolerance in the art, for example, within 2 standard deviations of the mean. Unless otherwise clear from the context, all numerical values provided herein are modified by the term about.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Theodorou D, Ayazi S, DeMeester S R, et al. Intraluminal pH and goblet cell density in Barrett's esophagus. J Gastrointest Surg 2012; 16:469-74
2. Siersema P D. Esophageal cancer. Gastroenterol Clin North Am 2008; 37:943-64
3. Domper M J, Ferrandez A A, Lanas A. Esophageal cancer: Risk factors, screening and endoscopic treatment in Western and Eastern countries. World J Gastroenterol 2015; 21:7933-43
4. Wani S, Rubenstein J H, Vieth M, et al. Diagnosis and management of low-grade dysplasia in Barrett's esophagus: expert review from the Clinical Practice Updates Committee of the American Gastroenterological Association. Gastroenterology 2016; 151:822-35
5. Hvid-Jensen F, Pedersen L, Drewes A M, et al. Incidence of adenocarcinoma among patients with Barrett's esophagus. N Engl J Med 2011; 365:1375-83

6. Snider E J, Freedberg D E, Abrams J A. Potential role of the microbiome in Barrett's esophagus and esophageal adenocarcinoma. Dig Dis Sci 2016; 61:2217-2225
7. Yang L, Lu X, Nossa C W, et al. Inflammation and intestinal metaplasia of the distal esophagus are associated with alterations in the microbiome. Gastroenterology 2009; 137:588-597
8. Okereke I C, Hamilton C, Reep G, et al. Microflora composition in the gastrointestinal tract in patients with Barrett's esophagus. J Thorac Dis 2019; 11:S1581-S1587.
9. Amir I, Konikoff F M, Oppenheim M, et al. Gastric microbiota is altered in oesophagitis and Barrett's oesophagus and further modified by proton pump inhibitors. Environ Microbiol 2014; 16:2905-14
10. di Pietro M, Chan D, Fitzgerald R C, et al. Screening for Barrett's esophagus. Gastroenterology 2015; 148:912-23
11. Klindworth A, Pruesse E, Schweer T, et al. Evaluation of general 16S ribosomal RNA gene PCR primers for classical and next-generation sequencing-based diversity studies. Nucleic Acids Res 2013; 41:e1.
12. Blankenburg D, Gordon A, Von Kuster G, et al. Manipulation of FASTQ data with Galaxy. Bioinformatics 2010; 26:1783-85
13. Yilmaz P, Parfrey L W, Yarza P, et al. The SILVA and "All-species Living Tree Project (LTP)" taxonomic frameworks. Nucleic Acids Res 2014; 42:D643-8
14. Langmead B, Salzberg S L: Fast gapped-read alignment with Bowtie 2. Nat Methods 2012; 9(4):357-9
15. Yang L, Chaudhary N, Baghdadi J, et. al. Microbiome in reflux disorders and esophageal adenocarcinoma. Cancer J 2014; 20:207-210
16. Kaakoush N, Morris M. The oesophageal microbiome: an unexplored link in obesity-associated oesophageal adenocarcinoma. FEMS Microbiol Ecol 2016; 92(10). pii: fiw161.doi:10.1093/femsec/fiw161
17. Paull G, Yardley J. Gastric and esophageal *Campylobacter pylori* in patients with Barrett's esophagus. Gastroenterol 1988; 95:216-218
18. Deshpande N, Riordan S, Castano-Rodriguez N, et. al. Signatures within the esophageal microbiome are associated with host genetics, age, and disease. Microbiome 2018; 6:227
19. Blackett K L, Siddhi S S, Cleary S, et al. Oesophageal bacterial biofilm changes in gastro-oesophageal reflux disease, Barrett's and oesophageal carcinoma: association or causality? Aliment Pharmacol Ther 2013; 37:1084-1092
20. Pei Z, Bini E J, Yang L, et al. Bacterial biota in the human distal esophagus. Proc Natl Acad Sci 2004; 101: 4250-4255
21. Okereke I C, Miller A, Hamilton C, et al. Microbiota of the oropharynx and endoscope compared to the esophagus. Sci Rep 2019 Jul. 15; 9(1):10201. doi: 10.1038/s41598-019-46747-y
22. Huang C H, Yu X, Liao W. The expensive-tissue hypothesis in vertebrates: Gut microbiota effect, a review. Int J Mol Sci 2018; 19. doi: 10.3390/ijms19061792
23. Munch N S, Fang H, Ingermann J, et al. High-fat diet accelerates carcinogenesis in a mouse model of Barrett's esophagus via IL-8 and alterations to the gut microbiome. Gastroenterol 2019; 157:492-506
24. Zackular J P, Baxter N T, Iverson K D, et al. The gut microbiome modulates colon tumorigenesis. Mbio 2013; 4:e00692-13
25. Okereke I C, Hamilton C, Wenholz A, et al. Associations of the microbiome and esophageal disease. J Thorac Dis 2019; 11:S1588-S1593
26. Richter J E, Rubenstein J H. Presentation and epidemiology of gastroesophageal reflux disease. Gastroenterology 2018; 154:267-76
27. Mosavi-Jarrahi A, Mohagheghi M. Epidemiology of esophageal cancer in the high-risk population of Iran. Asian Pacific J Cancer Prev 2006; 7(3):375-80
28. Lynch S, Pedersen O. The human intestinal microbiome in health and disease. N Engl J Med 2016; 375:2369-79
29. Devaraj S, Hemarajata P, Versalovic J. The human gut microbiome and body metabolism: implications for obesity and diabetes. Clin Chem 2013; 59:617-28
30. Martinez K, Leone V, Chang E. Western diets, gut dysbiosis, and metabolic diseases: Are they linked? Gut Microbes 2017; 8:130-142
31. Kaakoush N, Lecomte V, Maloney C A, et al. Cross-talk among metabolic parameters, esophageal microbiota, and host gene expression following chronic exposure to an obesogenic diet. Sci Rep 2017 Mar. 31; 7:45753.
32. Hayakawa Y, Chang W, Jin G, et al. Gastrin and upper GI cancers. Curr Opin Pharmacol 2016; 31:31-37
33. Elias P S, Castell D O. The role of acid suppression in Barrett's esophagus. Am J Med 2017; 130:525-9
34. Snider E J, Compres G, Freedberg D E, et al. Barrett's esophagus is associated with a distinct oral microbiome. Clin Transl Gastroenterol 2018; 9:135
35. Lv J, Guo L, Liu J J, et al. Alteration of the esophageal microbiota in Barrett's esophagus and esophageal adenocarcinoma. World J Gastroenterol 2019; 25:2149-61
36. Di Pilato V, Freschi G, Ringressi M N, et al. The esophageal microbiota in health and disease. Ann N Y Acad Sci 2016; 1381:21-33

What is claimed is:

1. A method of treating a patient suspected of having Barrett's esophagus comprising:

obtaining a biological sample from an esophagus of the patient, wherein the sample is obtained from a proximal or a distal esophagus;

determining a microbiome in the biological sample by detecting the presence of bacteria by plasmid dilution verification or quantitative polymerase chain reaction (qPCR), wherein an absence of *Corynebacterium, Dialister, Gemella, Haemophilus, Leptotrichia, Neisseria, Prevotella*, or *Rothia*, is indicative of worsened severity of Barrett's esophagus;

determining an absence of bacteria selected from *Corynebacterium, Dialister, Gemella, Haemophilus, Leptotrichia, Neisseria, Prevotella*, or *Rothia* that is indicative of worsened severity of Barrett's esophagus; and administering to the patient with worsened severity of Barrett's esophagus a probiotic therapy selected from at least one of *Corynebacterium, Dialister, Gemella, Haemophilus, Leptotrichia, Neisseria, Prevotella*, or *Rothia.*

2. The method of claim 1, further comprising stratifying patients based on the presence of bacteria in the proximal esophagus and distal esophagus.

3. The method of claim 1, wherein a decrease in *Streptococcus vestibularis* is indicative of Barrett's esophagus.

4. The method of claim 1, wherein the absence of *Actinomyces*, and *Prevotella pallens* at the proximal esophagus is indicative of Barrett's esophagus.

5. The method of claim 1, wherein the absence of *Dialister, Prevotella* unspecified, and *Streptococcus salivarius* at the distal esophagus is indicative of Barrett's esophagus.

6. The method of claim 1, wherein the worsened severity of Barrett's esophagus is determined without use of age, gender or presence of hiatal hernia as a factor or factors.

7. A method of determining an extent of disease progression in a patient suspected of having Barrett's esophagus comprising:

obtaining a biological sample from a proximal or a distal esophagus of the patient;

determining a microbiome in the biological sample by detecting the presence of bacteria by plasmid dilution verification or quantitative polymerase chain reaction (qPCR) at the one or more locations of the esophagus of the patient;

matching the extent of Barrett's esophagus to disease progression by detecting the presence of microorganisms at the one or more locations of the esophagus wherein an absence of *Corynebacterium, Dialister, Gemell*a, *Haemophilus, Leptotrichia, Neisseria, Prevotella*, or *Rothia*, is indicative of worsened severity of Barrett's esophagus determining an absence of *Corynebacterium, Dialister, Gemell*a, *Haemophilus, Leptotrichia, Neisseria, Prevotella*, or *Rothia* that is indicative of worsened severity of Barrett's esophagus; and administering to the patient with a, a worsened severity of Barrett's esophagus a probiotic therapy selected from at least one of *Corynebacterium, Dialister, Gemella, Haemophilus, Leptotrichia, Neisseria, Prevotella*, or *Rothia.*

8. The method of claim 7, wherein a decrease in *Streptococcus vestibularis* is indicative of Barrett's esophagus.

9. The method of claim 7, wherein the absence of *Actinomyces*, and *Prevotella pallens* at the proximal esophagus is indicative of Barrett's esophagus.

10. The method of claim 7, wherein the absence of *Dialister, Prevotella* unspecified, and *Streptococcus salivarius* at the distal esophagus is indicative of Barrett's esophagus.

11. The method of claim 7, wherein the biological sample is obtained from the distal esophagus and a length of a Barrett's column correlated with a level of Barrett's esophagus leading to esophageal cancer.

12. The method of claim 7, wherein the presence of Barrett's esophagus is determined without use of age, gender or presence of hiatal hernia as a factor or factors.

13. A method of treating a patient suspected of having Barrett's esophagus comprising:

obtaining or having obtained a biological sample from a proximal or a distal esophagus of the patient;

determining a microbiome indicative of worsened severity of Barrett's esophagus in the biological sample by detecting the presence of bacteria by plasmid dilution verification or quantitative polymerase chain reaction (qPCR), wherein an absence of bacteria selected from *Corynebacterium, Dialister*, Gemella, *Haemophilus, Leptotrichia, Neisseria, Prevotella*, or *Rothia* is indicative of worsened severity of Barrett's esophagus; and administering to the patient with worsened severity of Barrett's esophagus a probiotic therapy selected from at least one of *Corynebacterium, Dialister, Gemella, Haemophilus, Leptotrichia, Neisseria, Prevotella*, or *Rothia.*

* * * * *